US007078491B1

(12) United States Patent
Harrington

(10) Patent No.: US 7,078,491 B1
(45) Date of Patent: Jul. 18, 2006

(54) SELECTIVE BINDING AGENTS OF TELOMERASE

(75) Inventor: Lea A. Harrington, Toronto (CA)

(73) Assignee: Amgen Inc., Thousand Oaks, CA (US)

( * ) Notice: Subject to any disclaimer, the term of this patent is extended or adjusted under 35 U.S.C. 154(b) by 521 days.

(21) Appl. No.: 09/957,157

(22) Filed: Sep. 20, 2001

Related U.S. Application Data

(60) Provisional application No. 60/234,441, filed on Sep. 21, 2000.

(51) Int. Cl.
*C07K 16/00* (2006.01)
*C12P 21/08* (2006.01)

(52) U.S. Cl. .............................. 530/387.1; 530/387.3; 530/387.7; 530/388.26; 530/388.8; 530/389.1; 530/389.7

(58) Field of Classification Search ............. 530/386.1, 530/387.1, 387.3, 387.7, 388.26, 388.8, 389.1, 530/389.7
See application file for complete search history.

(56) References Cited

FOREIGN PATENT DOCUMENTS

| EP | 990701 A1 | 4/2000 |
|---|---|---|
| WO | WO 96/19580 | 6/1996 |
| WO | WO 98/14592 | 4/1998 |
| WO | WO 98/14593 | 4/1998 |
| WO | 98/37181 | * 8/1998 |
| WO | WO 99/01560 | 1/1999 |
| WO | WO 99/27113 | 6/1999 |
| WO | WO 99/50407 | 10/1999 |

OTHER PUBLICATIONS

Gura (Science, 1997, 278:1041-1042).*
Freshney (Culture of Animal Cells, A Manual of Basic Technique, Alan R. Liss, Inc., 1983, NY, p. 4).*
Pluckthun (Immunological Reviews, 1992, 19:151-188).*
Dermer (Bio/Technology, 1994, 12:390).*
Johnstone and Thorpe (Immunochemistry in Practice, Blackwell Scientific Publications, Oxford, 1987, pp. 49-50).*
Beattie et al., Reconstitution of Human Telomerase Activity in vitro, *Curr. Biol.*, 8:177-80 (1998).
Blasco et al., Telomere Shortening and Tumor Formation by Mouse Cells Lacking Telomerase RNA, *Cell*, 91:25-34 (1997).
Blasco et al., Differential Regulation Of Telomerase Activity and Telomerase RNA During Multi-Stage Tumorigenesis, *Nature Genetics*, 12:200-204 (1996).
Bodner et al., Extension of Life-Span by Introduction of Telomerase into Normal Human Cells, *Science* 279:349-352 (1998).

Chiu et al., Differential Expression of Telomerase Activity in Hematopoietic Progenitors from Adult Human Bone Marrow, *Stem Cells*, 14:239-248 (1996).
Greenberg et al., Short Dysfunctional Telomeres Impair Tumorigenesis in the INK4a$^2$/$^3$ Cancer-Prone Mouse, *Cell*, 97:515-525 (1999).
Greider et al., Telomeres and Telomerase in Cell Senescence and Immortalization, in *Cellular Aging and Cell Death*, Wiley-Liss Inc., New York, NY, pp. 123-138 (1996).
Greider, Telomere Length Regulation, *Annu. Rev. Biochem.*, 65:337-365 (1996).
Hahn et al., Inhibition of Telomerase Limits the Growth of Human Cancer Cells, *Nat. Med.*, 5:1164-1170 (1999).
Harley et al., Telomeres Shorten During Ageing of Human Fibroblasts, *Nature*, 345:458-460 (1990).
Harley et al., Telomerase, Cell Immortality, and Cancer, *Cold Spring Harbor Symposium on Quantitative Biology*, 59:307-315 (1994).
Harrington et al., Human Telomerase Contains Evolutionarily Conserved Catalytic And Structural Subunits, *Genes and Dev.*, 11:3109-3115 (1997).
Herbert et al., Inhibition of Human Telomerase in Immortal Human Cells Leads To Progressive Telomere Shortening and Cell Death, *Proc. Natl. Acad. Sci.*, 96:14276-14281 (1999).
Kilian et al., Isolation of a Candidate Human Telomerase Catalytic Subunit Gene, Which Reveals Complex Splicing Patterns in Different Cell Types, *Hum. Mol. Gen.*, 6:2011-2019 (1997).
Kohler et al., Continuous Cultures of Fused Cells Secreting Antibody of Predefined Specificity, *Nature*, 256:495-497 (1975).
Lendvay et al., Senescence Mutants of *Saccharomyces cerevisiae* with a Defect in Telomere Replication Identify Three Additional EST Genes, *Genetics*, 144:1399-1412 (1996).
Levy et al., Telomere End-replication Problem and Cell Aging, *J. Mol. Biol.*, 225:951-960 (1992).
Lingner et al., Reverse Transcriptase Motifs in the Catalytic Subunit of Telomerase, *Science*, 276:561-567 (1997).
Meyerson et al., hEST2, the Putative Human Telomerase Catalytic Subunit Gene, Is Up-Regulated in Tumor Cells and during Immortalization, *Cell*, 90:785-795 (1997).

(Continued)

*Primary Examiner*—Susan Ungar
(74) *Attorney, Agent, or Firm*—Marshall, Gerstein & Borun LLP

(57) ABSTRACT

The present invention relates to novel selective binding agents including polyclonal and monoclonal antibodies that recognize and bind to the catalytic subunit of human telomerase (hTERT). The invention also relates to the production, diagnostic use, and therapeutic use of the hTERT antibodies and fragments thereof.

19 Claims, 5 Drawing Sheets

OTHER PUBLICATIONS

Nakamura et al., Telomerase Catalytic Subunit Homologs from Fission Yeast and Human, *Science*, 277: 955-959 (1997).

Nakayama et al., Telomerase Activation By hTRT In Human Normal Fibroblasts and Hepatocellular Carcinomas, *Nature Gen.*, 18: 65-68 (1998).

Ogoshi et al., *In Situ* Hybridization Analaysis of the Expression of Human Telomerase RNA in Normal and Pathologic-Conditions of the Skin, *J. Invest. Dermatol.*, 110:818-23 (1998).

Oulton et al., Telomeres, Telomerase, and Cancer: Life of the Edge Of Genomic Stability, *Curr. Opin. in Oncol.*, 12: 74-81 (2000).

Robinson et al., Telomerase: A Reverse Transcriptase Essential for Genome Stability, *Biotech. Med.*, 12:6-9 (1998).

Taylor et al., Detection of Telomerase Activity in Malignant and Nonmalignant Skin Conditions, *J. Invest. Dermatol.* 106:759-765 (1996).

Vaziri et al., Reconstitution of Telomerase Activity in Normal Human Cells Leads To Elongation of Telomeres and Extended Replicative Life Span, *Curr. Biol.*, 8: 279-282 (1998).

Weinrich et al., Reconsitution of Human Telomerase with the Template RNA Component hTR and the Catalytic Protein Subunit hTRT, *Nat. Gen.*, 17: 498-502 (1998).

Zakian, Life and Cancer Without Telomerase, *Cell*, 91:1-3 (1997).

Zhang et al., Telomere Shortening And Apoptosis In Telomerase-Inhibited Human Tumor Cells, *Genes Dev.*, 13: 2388-2399 (1999).

* cited by examiner

FIG. 4A

Met Ser Thr Glu His Arg His Leu Thr Met Asn Phe Gly Phe Arg Leu
 1           5                   10                  15

Ile Phe Leu Val Leu Val Leu Lys Gly Val Gln Cys Glu Val Lys Leu
             20              25                  30

Val Glu Ser Gly Gly Gly Leu Val Lys Pro Gly Gly Ser Leu Lys Leu
         35              40                  45

Ser Cys Ala Ala Ser <u>Gly Phe Thr Phe Ser Ser Tyr Ala Met Ser</u> Trp
     50              55                  60

Val Arg Gln Thr Pro Glu Lys Arg Leu Glu Trp Val Ala S<u>er Ile Ser</u>
 65              70                  75                  80

<u>Ser Gly Gly Asn Thr Tyr Tyr Pro Asp Asn Val Gln Gly</u> Arg Phe Thr
             85                  90                  95

Ile Ser Arg Asp Asn Ala Arg Asn Ile Leu Tyr Leu Gln Met Ser Ser
            100                 105                 110

Leu Arg Ser Glu Asp Thr Ala Met Phe Tyr Cys Ala Arg G<u>lu Gly Val</u>
            115                 120                 125

<u>Tyr Asp Thr Tyr Gly Gly Val Asp Tyr</u> Trp Gly Gln Gly Thr Thr Leu
            130                 135                 140

Thr Val Ser Ser Ala Lys Thr Thr Pro Pro Ser Val Tyr Pro Leu Ala
145             150                 155                 160

Pro Gly Cys Gly Asp Thr Thr Gly Ser Ser Val Thr Leu Gly Cys Leu
            165                 170                 175

Val Lys Gly Tyr Phe Pro Glu Ser Val Thr Val Thr
            180                 185     188

FIG. 4B

| | | | | | | | | | | | | | | |
|---|---|---|---|---|---|---|---|---|---|---|---|---|---|---|

Met Glu Thr Asp Thr Ile Leu Leu Trp Val Leu Leu Leu Trp Val Pro
1               5                   10                  15

Gly Ser Thr Gly Asp Ile Val Leu Thr Gln Ser Pro Thr Ser Leu Ala
            20                  25                  30

Val Ser Leu Gly Gln Arg Ala Thr Ile Ser Cys <u>Lys Ala Ser Gln Ser</u>
        35                  40                  45

<u>Val Asp Tyr Asp Gly Asp Ser Phe Ile Asn</u> Trp Tyr Gln Gln Thr Pro
        50                  55                  60

Gly Gln Pro Pro Lys Leu Leu Ile Tyr <u>Ala Ala Ser Asn Leu Ala Ser</u>
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Asp Ala Ala Thr Tyr Tyr Cys
            100                 105                 110

<u>Gln Gln Ser Asn Glu Ala Pro Pro Thr</u> Phe Gly Gly Gly Thr Lys Leu
            115                 120                 125

Glu Ile Lys Arg Ala Asp Ala Ala Pro Thr Val Ser Ile Phe Pro Pro
            130                 135                 140

Ser Ser Glu Gln Leu Thr Ser Gly Gly Ala Ser Val Val Cys Phe Leu
145                 150                 155                 160

SELECTIVE BINDING AGENTS OF TELOMERASE

The present application claims priority benefit of U.S. Provisional Application No. 60/234,441 filed on Sep. 21, 2000, now abandoned, which is incorporated herein by reference in its entirety.

FIELD OF INVENTION

The present invention relates to antibodies that recognize and bind to the catalytic subunit of human telomerase (hTERT). More specifically, the invention relates to the production, diagnostic use, and therapeutic use of monoclonal antibodies and fragments thereof, which are specific towards the catalytic subunit of hTERT.

BACKGROUND

Many physiological changes occur as humans age. In addition to phenotypic changes, such as change in hair color, appearance of skin, and decreased lean body mass, many changes occur at the cellular and biochemical levels. One such change is the marked decrease in telomere length as somatic cells age (Harley et al., *Nature*, 345:458–460 [1990]). Telomeres are highly conserved repetitive DNA sequences localized at the ends of every chromosome, which comprise tandem repeats of specific GT-rich motifs. Telomeres are necessary for proper chromosome maintenance and replication. In addition, telomeres play a role in chromosomal localization within the cell nucleus. Telomeres are essential for cell viability as they protect chromosomes from degradation and recombination.

In most organisms, telomeres are synthesized and maintained by the enzyme telomerase. Telomerase is a multisubunit ribonucleoprotein which consists of one RNA component and two protein subunits. Both the RNA and protein components are necessary for telomerase activity (See, e.g., Greider, *Annu. Rev. Biochem.*, 65:337–365 [1996]; Greider et al., in *Cellular Aging and Cell Death*, Wiley-Liss Inc., New York, N.Y., pp. 123–138 [1996]). The catalytic subunit exhibits reverse transcriptase activity and utilizes the RNA template to catalyze the addition of telomeric DNA to chromosomal ends.

Most cells in adult humans do not exhibit telomerase activity; exceptions include, e.g., germ line tissues (sperm cells and oocytes) and certain blood cells (Greider et al., *Cellular Aging and Cell Death*, supra). Also, somatic stem or progenitor cells and activated lymphocytes exhibit telomerase activity that is typically either very low or only transiently active (Chiu et al., *Stem Cells* 14:239 [1996]).

There is evidence demonstrating a relationship between telomere length and cellular proliferation. Most normal somatic cells lack telomerase activity, and therefore the telomeres in these cells consistently shorten with subsequent divisions. This consistent shortening results in a finite life span for normal cells. Expression of hTERT in somatic cells will reverse the finite lifespan. (Bodner et al., *Science* 2: 349–352 [1998]; Vaziri et al., *Curr. Biol.* 8: 279–282 [1998]). The majority of immortal cell lines and tumor cells exhibit telomerase activity and the chromosomes in these cells maintain a stable telomere length as the cells divide in culture. (See Robinson & Harrington, *Biotech Med.*, 12:6–9 [1998]). Accordingly, constitutive expression of hTERT in normal cells, which endogenously express telomerase RNA, will establish telomerase activity. These studies establish telomere maintenance, carried out by hTERT, is critical for cell survival (Oulton and Harrington, *Curr. Opin. in Oncol.*, 12: 74–81 [2000]).

The relationship that exists between the maintenance of telomere length (i.e. telomerase activity) and cellular proliferation suggests that inhibition of telomerase activity may decrease tumor cell proliferation and provide potential cancer therapies. (Harley et al., *Cold Spring Harbor Symposium on Quantitative Biology*, supra; and Greider et al., *Cellular Aging and Cell Death*, supra.). In mouse tumor models, an increase in telomerase RNA has been shown to correlate with increased tumor progression (Blasco et al., *Nature Genetics*, 12:200–204 [1996]). In addition, inhibition of telomerase activity in cancer cells has been shown to cause telomere shortening, cell death and in some cases loss of the tumorigenic phenotype. (See Zhang et al., *Genes Dev.*, 13: 2388–2399 [1999]; Hahn et al., *Nat. Med.* 5: 1164–1170 [1999]; Herbert et al., *Proc. Natl. Acad. Sci.*, 96: 14276–14281 [1999]).

However, cells from telomerase RNA-deficient mice apparently lack telomerase activity, but purportedly these cells can be immortalized in culture and are able to generate tumors. See Blasco et al (*Cell*, 91:25–34 [1997]; see also Zakian, *Cell*, 91:1–3 [1997]). Further studies have indicated that late generations of mice doubly null for the INK4a (which encodes $p16^{INKa}$ and $p19^{ARF}$) and telomerase have a lower incidence of tumor formation and their cells form fewer foci in transformation assays. (Greenberg et al, *Cell*, 97: 515–525 [1999]). These results demonstrate that telomerase activity or hTERT expression alone does not confer a tumorigenic phenotype. Instead these results suggest that hTERT activity in combination with other oncogenic factors, such as inactivation of the pRB/p16 pathway or expression of viral oncogenes may cause immortalization in come cell types. (See Oulton & Harrington *Curr. Opin. Oncol.* 12: 74–81 [1999]).

Telomerase activity has also been detected in non-malignant hyperproliferative conditions such as psoriasis and contact dermatitis. (Taylor et al., *J. Invest. Dermatol.* 106: 759–65 [1996]; Ogoshi et al., *J. Invest. Dermatol.* 110: 818–23, [1998]). In addition, the level of telomerase activity within these lesions does not correlate with the level of inflammation, suggesting that the detected telomerase activity is associated with cellular proliferation within the lesion and not tissue inflammation.

Shortened telomeres are postulated to result in cellular senescence by preventing or inhibiting cellular division (Harley, supra; Levy et al., *J. Mol. Biol.*, 225:951–960 [1992]; and Harley et al., *Cold Spring Harbor Symposium on Quantitative Biology*, 59:307–315 [1994]). For example, the telomeres of $CD28^-/CD8^+$ T-cells, (which have a shorter life span in AIDS patients) are significantly shorter in AIDS patients as compared with the same cell-type obtained from healthy persons of the same or similar age (Effros et al., *AIDS*, 10: 17–22 [1996]). This study indicates that the shortened telomeres in the white blood cells of AIDS patients may be associated with the rapid senescence of these cells during the progression of the disease.

The human cDNA encoding the putative telomerase catalytic protein subunit has also been cloned (Harrington et al., *Genes and Dev,* 11: 3109–15 [1997]; Kilian et al., *Hum. Mol. Gen.*, 6: 2011–9 [1997]; Meyerson et al., *Cell*, 90:785–795 [1997]; Nakamura et al., *Science* 277: 955–959 [1997]). The hTERT protein was designated hTERT by HUGO Nomenclature Committee of the Genome Database. This protein shares significant sequence similarity with the catalytic subunit of telomerase from *Saccharomyces cerevisiae*

(EST2) (Lendvay et al., *Genetics,* 144:1399–1412 [1996]) *Schizosaccharomyces pombe* (TRT1) (Nakamura et al., *Science,* 277:955–959 [1997]) and *Euplotes aediculatus* (p123) (Linger et al., *Science,* 276:561–567 [1997]). hTERT mRNA has been detected in cancer cell lines and tumors which exhibit telomerase activity. Further, hTERT mRNA expression is induced upon telomerase activation, which occurs during cellular immortalization. Similarly, hTERT mRNA expression is down-regulated along with telomerase activity during human HL-60 promyelocytic leukemia cell differentiation. (Meyerson et al., *Cell,* 90:785–795 [1997]). The catalytic subunit is proposed to be the rate limiting determinant of telomerase activity (Nakayama et al., *Nature Gen.* 18: 65–8 [1998]; Weinrich et al., *Nat. Gen.,* 17: 498–502, [1998]; Beattie et al., *Curr. Biol.* 8: 177–80 [1998]).

Various reports describe antibodies which bind to telomerase. WO 98/14592 describes murine and rabbit polyclonal antibodies raised against the 43 kD subunit of telomerase. Publication WO 98/14593 describes anti-hTRT (human telomerase reverse transcriptase) antibodies raised against hTRT peptides and fusion proteins. WO 99/50407 (EP 990701A1) describes monoclonal antibodies that bind to human telomerase catalytic subunit (hTERT). The antibodies include monoclonal antibodies produced by hybridoma cell lines and recombinant monoclonal antibodies. WO 99/01560 generally describes antibodies against telomerase proteins and their subunits. WO 96/19580 describes rabbit polyclonal antibodies directed towards the two polypeptide subunits, the 80 kD and 95 kD polypeptide of *Tetrahymena* telomerase. In addition, this reference describes use of these antibodies to screen for telomerase proteins in humans and mice. WO 99/27113 discusses in general terms the production of antibodies against mouse telomerase and its subunits. Harrington et al., *Genes & Development* (1997) discuss the use of hTERT (human catalytic subunit of telomerase) antisera to detect telomerase activity and to purify hTERT from HeLa cells.

Yet there is still an undeveloped need to identify new specific binding agents to telomerase. These new specific binding agents may be particularly specific for the human version of the catalytic subunit of telomerase. Preferably, the specific binding agents will be a monoclonal or polyclonal antibody or a fragment thereof, which retains the binding function of the antibody. Such binding agents will be useful in screening for diseases that are associated with telomerase activity. A class of these new specific binding agents will bind and inhibit telomerase activity; therefore providing a therapeutic for telomerase associated diseases.

SUMMARY OF THE INVENTION

The present invention provides agents that selectively and specifically bind to telomerase. Optionally the agents selectively and specifically bind to the catalytic subunit of human telomerase (hTERT).

The present invention provides a hybridoma cell line and the monoclonal antibodies produced therefrom, which recognize and bind to the human telomerase catalytic subunit (hTERT). The invention also provides for the hTERT specific antibodies and fragments thereof which comprise an antibody-binding domain of a monoclonal antibody which specifically binds to the catalytic subunit of human telomerase. The hTERT specific antibodies and fragments thereof include those comprising whole antibodies, a human Fc region, fully human, antibodies, humanized antibodies, chimeric antibodies, CDR grafted antibodies, single chain variable fragments of the hTERT specific antibody, single chain Fv fragments of the hTERT specific antibody, such as heavy chain variable regions of the antibody, light chain variable regions, Fab fragments of the antibody and other antibody fragments which bind to hTERT. In addition, the invention provides for antibodies which inhibit telomerase catalytic activity.

Also provided by the present invention are isolated and purified polynucleotides encoding an antibody or fragment thereof comprising the antigen-binding domain of a monoclonal antibody that specifically binds to the catalytic subunit of human telomerase. These isolated and purified polynucleotides include polynucleotides encoding an antibody or fragment thereof wherein the heavy chain constant region is encoded by the polynucleotide set out as SEQ ID NO: 1 and/or the light chain constant region is encoded by the polynucleotide sequence set out as SEQ ID NO: 3. A further aspect of the present invention are vectors and host cells comprising the polynucleotide sequence encoding hTERT specific antibodies and fragments thereof, including those antibodies encoded by the polynucleotides set out as SEQ ID NOS: 1 and 3.

The present invention also provides for isolated and purified polypeptide antibodies or fragments thereof comprising an antigen-binding domain of a monoclonal antibody that specifically binds to the catalytic subunit of human telomerase. These isolated and purified polypeptide antibodies and fragments thereof include antibodies and fragments that have a heavy chain with the amino acid sequence set out as SEQ ID NO: 2 and/or the light chain has the amino acid sequence set out as SEQ ID NO: 4.

Another aspect of present invention is the diagnosis, prevention and/or treatment of various pathological consequences resulting from telomerase activity, hTERT activity or any related hTERT activities. Such pathological conditions include, but are not limited to, hyperproliferative conditions such as precancerous and hyperplastic conditions, cancer, psoriasis, contact dermatitis, immune disorders and inflammation. Methods of diagnosis include detecting the presence of hTERT with antibodies which specifically recognize or bind hTERT. Treatment methods include inhibiting telomerase activity by administering a hTERT specific binding agent, e.g., monoclonal antibodies specific for hTERT and fragments, variants and derivatives thereof. Treatment methods also include administering binding agents specific for human telomerase in combination with other therapeutic agents to enhance the therapeutic effects. These therapeutic agents include, but are not limited to, matrix metalloprotease inhibitor, intergrin antagonist, nonsteroidal anti-inflammatory drugs, cycooxygenase-2 inhibitor, radiation, and chemotherapetic agents. In addition, treatment methods also include hTERT specific antibodies conjugated to immunotoxins or radiolabels. The hTERT specific binding agents can be administered as pharmaceutical compositions alone or in the presence of the above-described therapeutic agents.

BRIEF DESCRIPTION OF THE FIGURES

FIGS. 4A–4B depicts the predicted amino acid sequences of the CDRs for the hTERT monoclonal antibody heavy and light chain (SEQ ID NOS: 2 and 4) respectively.

DETAILED DESCRIPTION OF INVENTION

Figure 1:
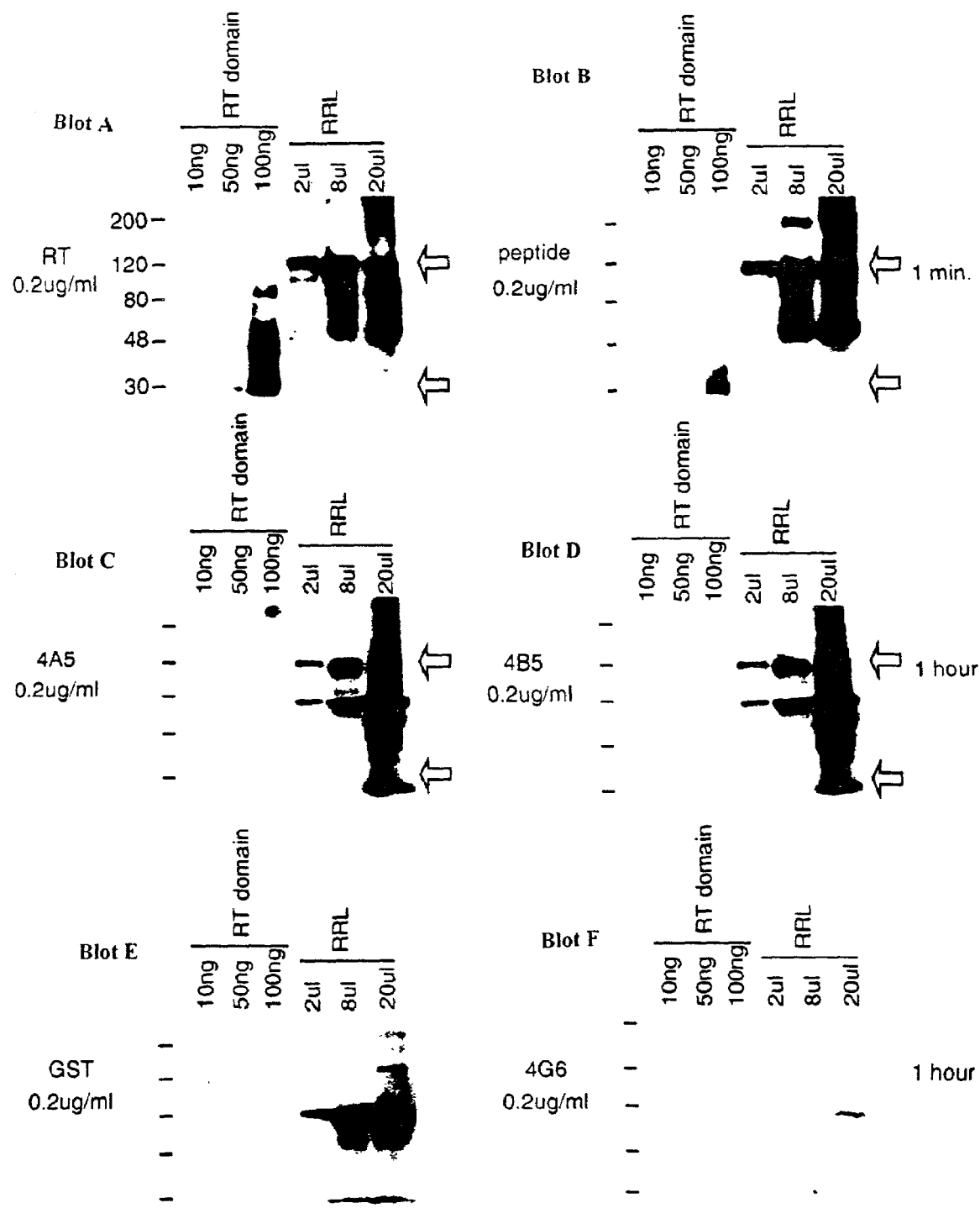
FIG. 1 depicts the Western blot analysis carried out to verify specificity of 4A5 and 4B5 monoclonal antibodies.

A human homolog of the catalytic subunit of telomerase has been identified and characterized as TP2 or hTERT (denoted herein as hTERT). Studies have shown that hTERT has a function similar to the catalytic telomerase subunits from *S. cervisiae* and *Euplotes*.

Definitions

The term "hTERT" refers to any polypeptide having the properties described herein for the catalytic subunit of human telomerase (hTERT). The hTERT polypeptide may or may not have an amino terminal methionine, depending on the manner in which it is prepared.

The term "selective binding agent" refers to a molecule which preferentially binds hTERT. A selective binding agent may be a protein, peptide, nucleic acid, carbohydrate, lipid, or small molecular weight compound which binds preferentially to hTERT. In a preferred embodiment, the selective binding agent according to the present invention is an antibody, such as polyclonal antibodies, monoclonal antibodies (mAbs), chimeric antibodies, CDR-grafted antibodies, humanized antibodies, anti-idiotypic (anti-Id) antibodies to antibodies that can be labeled in soluble or bound form, as well as fragments, regions or derivatives thereof, provided by known techniques, such techniques include, but are not limited to enzymatic cleavage, peptide synthesis or recombinant techniques. The anti-hTERT selective binding agents of the present invention are capable of binding portions of hTERT that inhibit the catalytic activity of hTERT and other hTERT-associated activities. These hTERT-associated activities include interactions with the telomerase RNA subunit, binding to nucleotides or other substrates, and cellular translocation.

The antibodies and antigen binding domains of the invention bind selectively to hTERT, which means they bind preferentially to hTERT with a greater binding affinity than they bind to other antigens. Typically, the anti-hTERT antibodies of the invention or fragments thereof of will bind with a greater affinity to the human catalytic subunit of telomerase as compared to its binding affinity to the catalytic subunit of telomerase of other species.

The term "monoclonal antibody" refers to an antibody obtained from a population of substantially homogeneous antibodies wherein each monoclonal antibody will typically recognize the same epitope on the antigen. The term "monoclonal" is not limited to any particular method for making the antibody. For example, monoclonal antibodies of the invention may be made by the hybridoma method as described in Kohler et al., *Nature* 256:495 [1975]. In an alternative embodiment, human antibodies can be produced from phage-display libraries (Hoogenboom et al., *J. Mol. Biol.* 227: 381 [1991]; Marks et al., *J. Mol. Biol.* 222: 581, [1991]; see also U.S. Pat. No. 5,885,793).

The term "antigen binding domain" or "antigen binding region" refers to that portion of the selective binding agent (such as an antibody molecule) which contains the amino acid residues that interact with an antigen and confer on the binding agent its specificity and affinity for the antigen.

The term "epitope" refers to that portion of any molecule capable of being recognized by and bound by a selective binding agent, e.g. an antibody, at one or more of the binding agent's antigen binding regions. Epitopes usually consist of chemically active surface groupings of molecules such as amino acids or carbohydrate side chains and have specific three dimensional structural characteristics as well as specific charge characteristics.

The term "inhibiting and/or neutralizing epitope" is an epitope, which, when bound by a selective binding agent such as an antibody, results in the loss of biological activity of the molecule, cell, or organism containing such epitope, in vivo, in vitro, or in situ. In the context of the present invention, the neutralizing epitope is located on or is associated with hTERT.

Antibodies comprise two functionally independent parts, a variable domain known as "Fab", which binds antigens, and a constant domain which comprises the carboxy terminal portion of the heavy and light chain and is known as "Fc", which is involved in effector functions such as complement activation and attack by phagocytic cells. An Fc domain may have a relatively long serum half-life, whereas an Fab is short-lived. (Capon et al., *Nature*, 337: 525–31 [1989]) When constructed together with a therapeutic protein, an Fc domain can provide longer half-life or incorporate such functions as Fc receptor binding, protein A binding, complement fixation and perhaps even placental transfer into the therapeutic protein to which it is attached. Id. The Fc region may be a naturally occurring Fc region, or may be altered to improve certain qualities, such as therapeutic qualities, circulation time, to reduce aggregation and other qualities.

The term "variable region" or "variable domain" refers to a portion of the light and/or heavy chains of an antibody, typically including approximately the amino-terminal 120 to 130 amino acids in the heavy chain and about 100 to 110 amino acids in the light chain, which differ extensively in sequence among antibodies and which determine the binding and specificity of each particular antibody for its particular antigen. The variability in sequence is concentrated in those regions called complementarity determining regions (CDRs) while the more highly conserved regions in the variable domain are called framework regions (FR). The CDRs of the light and heavy chains contain within them the amino acids which are largely responsible for the interaction of the antibody with antigen.

The term "light chain" when used in reference to an antibody refers to two distinct types, called kappa (k) or lambda (l) based on the amino acid sequence of the constant domains.

The term "heavy chain" when used in reference to an antibody refers to five distinct types, called alpha, delta, epsilon, gamma and mu, based on the amino acid sequence of the heavy chain constant domain. The combination of heavy and light chains give rise to five classes of antibodies: IgA, IgD, IgE, IgG and IgM, respectively, including four subclasses of IgG, which are $IgG_1$, $IgG_2$, $IgG_3$ and $IgG_4$.

The term "fragment" when used in relation to hTERT or antibodies that bind to hTERT refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may result from alternative RNA splicing or from in vivo or in vitro protease activity such fragments may also be constructed by recombinant DNA methods beginning with polynucleotides encoding the antibody. Such fragments, which retain the ability to bind to hTERT include for example Fab fragments, scFv (single chain antibody) and others.

The term "variant" when used in relation to hTERT or polypeptide selective binding agent which binds to hTERT refers to a peptide or polypeptide which binds to hTERT and which comprises one or more amino acid sequence substitutions, deletions, and/or additions as compared to a native or unmodified sequence. For example, a hTERT antibody variant may result from one or more changes to an amino acid sequence of native hTERT antibody. Another example of a variant is the result of one or more changes to an amino acid sequence of a previously unmodified fragment of hTERT antibody. Variants may be naturally occurring, such as allelic or splice variants, or may be artificially constructed. Polypeptide variants may be prepared from the corresponding nucleic acid molecules encoding said variants.

The term "derivative" when used in relation to hTERT or polypeptide selective binding agent which binds to hTERT refers to a polypeptide, or peptide, or a variant, fragment or derivative thereof, which has been chemically modified. Examples of such modifications include covalent attachment of one or more polymers, such as water soluble polymers, N-linked, or O-linked carbohydrates, sugars, phosphates, and/or other such molecules. The derivatives are modified in a manner that is different from naturally occurring or starting peptide or polypeptides, either in the type or location of the molecules attached. Derivatives further include deletion of one or more chemical groups which are naturally present on the peptide or polypeptide.

The term "fusion" when used in relation to hTERT or polypeptide selective binding agent which binds to hTERT refers to the joining of the peptide or polypeptide, or fragment, variant and/or derivative thereof, with a heterologous peptide or polypeptide. These heterologous polypeptides include, but are not limited to Fc regions of IgG, epitopes to allow for detection and isolation or which otherwise alter the activity of hTERT binding polypeptide, and enzymes or portions thereof which are catalytically active.

The term "chimeric" refers to an antibody in which a portion of the heavy and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass.

The term "CDR grafted" antibody refers to an antibody in which the a CDR from an antibody of a particular species or isotype is recombinantly inserted into the framework of an antibody of another species or isotype. The term "humanized" refers to an antibody in which the framework is derived from a human but the CDR will be replaced with that derived from another species such as a murine CDR.

The term "fully human" antibody refers to an antibody in which the CDR and the framework are derived from a human.

The term "biologically active" when used in relation to hTERT or a polypeptide selective binding agent against hTERT refers to a peptide or a polypeptide having at least one activity characteristic of hTERT or a selective binding agent of hTERT. The activity characteristic of a selective binding agent which binds to hTERT may be agonistic, antagonistic, or neutralizing or blocking activity with respect to at least one biological activity of hTERT. Preferably, the activity is antagonistic, neutralizing or blocking activity with respect to telomerase activity of hTERT.

The term "naturally occurring" when used in connection with biological materials such as nucleic acid molecules, polypeptides, host cells, and the like, refers to those which are found in nature and not modified by a human being. The term "isolated" when used in relation to hTERT or to a proteinaceous selective binding agent of hTERT refers to a peptide or a polypeptide that is free from at least one contaminating polypeptide that is found in its natural environment, and preferably substantially free from any other contaminating mammalian polypeptides which would interfere with its therapeutic or diagnostic use.

The term "mature" when used in relation to hTERT or to a proteinaceous selective binding agent of hTERT refers to a peptide or a polypeptide lacking a leader sequence.

The terms "effective amount" and "therapeutically effective amount" when used in relation to a selective binding agent of hTERT refers to an amount of a selective binding agent that is useful or necessary to support an observable change in the level of one or more biological activities of telomerase and/or hTERT. The change may be either an increase or decrease in the level of hTERT activity. Preferably, the change is a decrease in hTERT activity.

The term "conservative amino acid substitution" refers to a substitution of a native amino acid with a non-native amino acid such that there is a conservation of properties between the native amino acid residue at that position and the substituted amino acid. For example, a conservative substitution results from the replacement of a non-polar amino acid in a polypeptide with any other non-polar amino acid. Furthermore, any native amino acid in a polypeptide may also be substituted with alanine, as has been previously described for alanine scanning mutagenesis (Cunningham et al., *Science* 244:1081–1085 [1989]).

Diseases Involving Human Telomerase

The present invention provides for an antibody or fragment thereof that binds to hTERT (anti-hTERT antibody) which are useful for the treatment of human diseases and pathological conditions. The anti-hTERT antibodies of present invention, including polyclonal and monclonal antibodies expressed from hybridoma or by recombinant technology, can be used to induce or increase telomerase activity in a cell, or inhibit unwanted telomerase activity in a cell. By inhibiting, activating, or otherwise altering telomerase activity in a cell, the proliferative activity of a cell can be manipulated. For example, there is a correlation between telomerase levels and the behavior of cancer cells, indicating any reduction in telomerase activity could reduce the aggressive nature of tumor cells to a more easily treatable state, or even eliminate the disease. In addition, agents which reduce telomerase activity may be used in combination with other therapeutic agents to enhance their therapeutic effects or decrease potential side-effects.

In one aspect, the present invention provides reagents and methods useful for treating diseases and conditions characterized by the unwanted levels of human telomerase activity in a cell. These diseases include, cancers, and other hyperproliferative conditions, such as hyperplasia, psoriasis, contact dermatitis, immunological disorders, and infertility.

The present invention provides compositions and methods useful for the treatment of a wide variety of cancers, including solid tumors and leukemias. Types of cancer that may be treated include, but are not limited to: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include: histiocytic disorders; leukemia; histiocytosis malignant; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; tophoblastic tumor. Further, the following types of cancers may also be treated: adenoma; cholangioma; cholesteatoma; cyclindroma; cystadenocarcinoma; cystadenoma; granulosa cell tumor; gynandroblastoma; hepatoma; hidradenoma; islet cell tumor; leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include, but are not limited to the following: angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosareoma; ovarian carcinoma; rhabdomyosarcoma; sarcoma; neoplasms; nerofibromatosis; and cervical dysplasia. The invention further provides compositions and methods useful for treatment of other conditions in which cells have become immortalized or hyperproliferative due to abnormally high expression of hTERT.

Another aspect of the present invention is using the materials and methods of the present invention to prevent and/or treat any hyperproliferative condition of the skin including psoriasis and contact dermatitis or other hyperproliferative diseases. It has been demonstrated that patients with psoriasis and contact dermatitis have elevated telomerase activity within these lesions (Ogoshi et al, *J. Inv. Dermatol.*, 110:818–23 [1998]). Preferably, antibodies specific for hTERT will be used in combination with other pharmaceutical agents to treat humans that express these clinical symptoms. The antibody can be delivered using any of the various carriers through routes of administration described herein and others which are well known to those of skill in the art.

Another aspect of present invention is the prevention of cancers utilizing the compositions and methods provided by the present invention. Such reagents will include antibodies against hTERT.

hTERT Selective Binding Agents and Antibodies

As used herein, the term "selective binding agent" refers to a molecule which has specificity for one or more hTERT polypeptides. Suitable selective binding agents include, but are not limited to, antibodies and derivatives thereof, polypeptides, and small molecules. Suitable selective binding agents may be prepared using methods known in the art. An exemplary hTERT polypeptide selective binding agent of the present invention is capable of binding a certain portion of the hTERT polypeptide thereby inhibiting the activity or function of hTERT polypeptide.

Selective binding agents such as antibodies and antibody fragments that bind hTERT polypeptides are within the scope of the present invention. The antibodies may be polyclonal including monospecific polyclonal, monoclonal (MAbs), recombinant, chimeric, humanized such as CDR-grafted, human, single chain, and/or bispecific, as well as fragments, variants or derivatives thereof. Antibody fragments include those portions of the antibody which bind to an epitope on the hTERT polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward a hTERT polypeptide generally are produced in animals (e.g., rabbits or mice) by means of multiple subcutaneous or intraperitoneal injections of hTERT polypeptide and an adjuvant. It may be useful to conjugate a hTERT polypeptide to a carrier protein that is immunogenic in the species to be immunized, such as keyhole limpet heocyanin, serum, albumin, bovine thyroglobulin, or soybean trypsin inhibitor. Also, aggregating agents such as alum are used to enhance the immune response. After immunization, the animals are bled and the serum is assayed for anti-hTERT polypeptide antibody titer.

Monoclonal antibodies directed toward hTERT polypeptide are produced using any method which provides for the production of antibody molecules by continuous cell lines in culture. Examples of suitable methods for preparing monoclonal antibodies include the hybridoma methods of Kohler et al. (*Nature*, 256: 495–497, [1975]) as described herein and the human B-cell hybridoma method (Kozbor *J. Immunol.*, 133: 3001, [1984]; Brodeur et al., *Monoclonal Antibody Production Techniques and Applications*, pp. 51–63, Marcel Dekker, Inc., New York, [1987]). Also provided by the invention are hybridoma cell lines which produce monoclonal antibodies reactive with hTERT polypeptides.

Monoclonal and polyclonal antibodies of the invention may be modified for use as therapeutics. One embodiment is a "chimeric" antibody in which a portion of the heavy and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See, U.S. Pat. No. 4,816,567 and Morrison et al., *Proc. Natl. Acad. Sci. U.S.A.*, 81: 6851–6855 [1985].

In another embodiment, an antibody of the invention is a "humanized" antibody. Methods for humanizing non-human antibodies are well known in the art. (see U.S. Pat. Nos. 5,585,089, and 5,693,762). Generally, a humanized antibody has one or more amino acid residues introduced into its framework region from a source which is non-human. Humanization can be performed, for example, using methods described in the art (Jones et al., *Nature* 321: 522–525, [1986]; Riechmann et al., *Nature*, 332: 323–327, [1988]; Verhoeyen et al., *Science* 239:1534–1536, [1988]), by substituting at least a portion of a rodent complementarity-determining region (CDRs) for the corresponding regions of a human antibody.

Also encompassed by the invention are human antibodies which bind hTERT polypeptide, fragments, variants and/or derivatives. Using transgenic animals (e.g., mice) that are capable of producing a repertoire of human antibodies in the absence of endogenous immunoglobulin production such antibodies are produced by immunization with a hTERT antigen (i.e., having at least 6 contiguous amino acids), optionally conjugated to a carrier. See, for example, Jakobovits et al., *Proc. Natl. Acad. Sci. U.S.A.*, 90: 2551–2555, [1993]; Jakobovits et al., *Nature* 362: 255–258, [1993]; Bruggermann et al., *Year in Immuno.*, 7: 33, [1993]. In one method, such transgenic animals are produced by incapacitating the endogenous loci encoding the heavy and light immunoglobulin chains therein, and inserting loci encoding human heavy and light chain proteins into the genome thereof. Partially modified animals, that is those having less than the full complement of modifications, are then crossbred to obtain an animal having all of the desired immune system modifications. When administered an immunogen, these transgenic animals produce antibodies with human variable regions, including human (rather than e.g., murine) amino acid sequences, including variable regions which are immunospecific for these antigens. See PCT application Nos. PCT/US96/05928 and PCT/US93/06926. Additional methods are described in U.S. Pat. No. 5,545,807, PCT application Nos. PCT/US91/245, PCT/GB89/01207, and in EP 546073B1 and EP 546073A1. Human antibodies may also be produced by the expression of recombinant DNA in host cells or by expression in hybridoma cells as described herein.

Human antibodies could also, potentially, be produced by exposing human splenocytes (B or T cells) to an antigen in vitro, then reconstituting the exposed cells in an immunocompromised mouse, e.g. SCID or nod/SCID. See Brams et al., *J. Immunol.*, 160: 2051–2058 [1998]; Carballido et al., *Nat Med.*, 6: 103–106 [2000].

In an alternative embodiment, human antibodies can be produced from phage-display libraries (Hoogenboom et al., *J. Mol. Biol.* 227: 381 [1991]; Marks et al., *J. Mol. Biol.* 222: 581, [1991]). These processes mimic immune selection through the display of antibody repertoires on the surface of filamentous bacteriophage, and subsequent selection of phage by their binding to an antigen of choice. One such technique is described in PCT Application No. PCT/US98/17364, filed in the name of Adams et al., which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

In a further embodiment of the invention, the polypeptides comprising the amino acid sequence variable domains of hTERT antibodies, such as the heavy chain variable region with the amino acid sequence of SEQ ID NO: 2 or the light chain variable region with the amino acid sequence of SEQ ID NO: 4, is fused to one or more domains of an Fc region of human IgG. When constructed together with a therapeutic protein such as the Fab of hTERT specific antibodies, an Fc domain can provide longer half-life or incorporate such functions as Fc receptor binding, protein A binding, complement fixation and perhaps even placental transfer. (Capon et al., *Nature*, 337: 525–531, [1989])

In one example, all or a portion of the human IgG hinge, CH2 and CH3 regions may be fused at either the N-terminus or C-terminus of the hTERT polypeptides using methods known to the skilled artisan. The resulting hTERT fusion antibody may be purified by use of a Protein A or Protein G affinity column. Peptides and proteins fused to an Fc legion have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, reduce aggregation, etc. Other examples known in the art include the Fc of IgG1 fused to the N-terminus of CD30L to treat Hodkin's Disease, anaplastic lymphoma and T-cell leukemia (U.S. Pat. No. 5,480,981), the Fc region on IgG1 fused to the TNF receptor to treat septic shock (Fisher et al., *N. Engl. J. Med.*, 334: 1697–1702, [1996]), and the Fc of IgG1 fused to the Cd4 receptor to treat AIDS (Capon et al., *Nature*, 337: 525–31, [1989]).

Binding Assays

Immunological binding assays typically utilize a capture agent to bind specifically to and often immobilize the analyte (target). The capture agent is a moiety that specifically binds to the analyte. In one embodiment of the present invention, the capture agent is an antibody or fragment thereof that specifically binds to hTERT, which is produced by the methods of the present invention. These immunological binding assays are well known in the art (see, Asai, ed., Methods in Cell Biology, Vol. 37, *Antibodies in Cell Biology*, Academic Press, Inc., New York [1993]).

Immunological binding assays frequently utilize a labeling agent that will signal the existence of the bound complex formed by the capture agent and analyte. The labeling agent can be one of the molecules comprising the bound complex; i.e. it can be labeled hTERT or a labeled anti-hTERT antibody. Alternatively, the labeling agent can be a third molecule, commonly another antibody, which binds to the bound complex. The labeling agent can be, for example, an anti-hTERT antibody bearing a label. The second antibody, specific for the bound complex, may lack a label, but can be bound by a fourth molecule specific to the species of antibodies which the second antibody is a member of. For example, the second antibody can be modified with a detectable moiety, such as biotin, which can then be bound by a fourth molecule, such as enzyme-labeled streptavidin. Other proteins capable of specifically binding immunoglobulin constant regions, such as protein A or protein G may also be used as the labeling agent. These binding proteins are normal constituents of the cell walls of streptococcal bacteria and exhibit a strong non-immunogenic reactivity with immunoglobulin constant regions from a variety of species (see, generally Akerstrom, *J. Immunol.*, 135:2589–2542 [1985]; and Chaubert, *Mod. Pathol*, 10:585–591 [1997]).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures.

A. Non-Competitive Binding Assays:

Immunological binding assays can be of the non-competitive type. These assays have an amount of captured analyte, hTERT, that is directly measured. For example, in one preferred "sandwich" assay, the capture agent (anti-hTERT antibody) can be bound directly to a solid substrate where it is immobilized. These immobilized antibodies then capture (bind to) hTERT present in the test sample. The hTERT protein thus immobilized is then bound to a labeling agent, such as a second hTERT antibody having a label. In another preferred "sandwich" assay, the second hTERT antibody lacks a label, but can be bound by a labeled antibody specific to antibodies of the species from which the second hTERT antibody is derived. The second hTERT antibody also can be modified with a detectable moiety, such as biotin, to which a third labeled molecule can specifically bind, such as streptavidin. (See, Harlow and Lane, *Antibodies, A Laboratory Manual*, Ch 14, Cold Spring Harbor Laboratory, NY [1988], incorporated herein by reference).

B. Competitive Binding Assays:

Immunological binding assays can be of the competitive type. The amount of analyte, hTERT, present in the sample is measure indirectly by measuring the amount of an added analyte displaced, or competed away, from a capture agent by the analyte present in the sample. In one preferred competitive binding assay, a known amount of hTERT, usually labeled, is added to the sample and the sample is then contacted with an anti-hTERT antibody (the capture agent). The amount of labeled hTERT bound to the antibody is inversely proportional to the concentration of hTERT present in the sample. (See, Harlow and Lane, *Antibodies, A Laboratory Manual*, Ch 14 pp. 579–583, supra).

In another preferred competitive binding assay, the antibody is immobilized on a solid substrate. The amount of hTERT bound to the antibody may be determined either by measuring the amount of hTERT present in an hTERT/antibody complex, or alternatively by measuring the amount of remaining uncomplexed hTERT. The amount of hTERT may be detected by providing a labeled hTERT. See, Harlow and Lane, *Antibodies, A Laboratory Manual*, Ch 14, supra.).

Yet another preferred competitive binding assay, hapten inhibition is utilized. Here, a known analyte, hTERT, is immobilized on a solid substrate. A known amount of anti-hTERT antibody is added to the sample, and the sample is contacted with the immobilized hTERT. The amount of anti-hTERT bound to the immobilized hTERT is inversely proportional to the amount of hTERT present in the sample. The amount of immobilized antibody may be detected by detecting either the immobilized fraction of antibody or the fraction that remains in solution. Detection may be direct where the antibody is labeled or indirect by the subsequent addition of a labeled moiety that specifically binds to the antibody as described above.

C. Utilization of Competitive Binding Assays:

The competitive binding assays can be used for crossreactivity determinations to permit a skilled artisan to determine if a protein or enzyme complex is hTERT and not a cross-reacting molecule or to determine whether the antibody to hTERT is specific for hTERT and does not bind unrelated antigens. hTERT can be immobilized to a solid support. An unknown protein mixture is added to the assay, which will compete with the binding of the antibodies to the immobilized hTERT. The competing molecule also binds one or more antigens unrelated to hTERT. The ability of the proteins to compete with the binding of the antibodies to the immobilized hTERT is compared to the binding by the same hTERT that was immobilized to the solid support to determine the crossreactivity of the protein mix.

D. Other Binding Assays:

The present invention also provides Western blot methods to detect or quantify the presence of hTERT in a sample. The technique generally comprises separating sample proteins by gel electrophoresis on the basis of molecular weight and transferring the proteins to a suitable solid support, such as nitrocellulose filter, a nylon filter, or derivatized nylon filter. The sample is incubated with antibodies or fragments thereof that specifically bind hTERT. These antibodies may be directly labeled or alternatively may be subsequently detected using labeled antibodies that specifically bind to the anti-hTERT antibody.

Diagnostic Assays

The antibodies or fragments thereof of present invention are useful for the diagnosis of conditions or diseases characterized by expression of telomerase or telomerase protein subunits, or in assays to monitor patients being treated with inducers of telomerase, its fragments, agonists or inhibitors of telomerase activity. Diagnostic assays for telomerase include methods utilizing the antibody and a label to detecttelomerase in human body fluids or extracts of cells or tissues. The antibodies of the present invention can be used with or without modification. In a preferred diagnostic assay, the antibodies will be labeled by attaching a reporter molecule. A wide variety of reporter molecules are known, some of which have been already described herein. In particular, the present invention is useful for diagnosis of human disease.

A variety of protocols for measuring telomerase proteins using either polyclonal or monoclonal antibodies specific for the respective protein are known in the art. Examples include enzyme-linked immunosorbent assay (ELISA), radioimmunoassay (RIA) and fluorescence activated cell sorting (FACS). A two-site, monoclonal-based immunoassay utilizing monoclonal antibodies reactive to two noninterfering epitopes on hTERT is preferred, but a competitive binding assay can be employed. These assays are described, for example, in Maddox et al., *J. Exp. Med.*, 158:1211 [1983].

In order to provide a basis for diagnosis, normal or standard values for human telomerase or, specifically, hTERT expression are usually established. This is accomplished by combining body fluids or cell extracts taken from normal subjects, preferably human, with antibody to hTERT under conditions suitable for complex formation which are well known in the art. The amount of standard complex formation is quantified by comparing the binding of antihTERT antibodies to known quantities of hTERT protein, with both control and disease samples from biopsied tissues. Then, standard values obtained from normal samples are compared with values obtained from samples from subjects potentially affected by disease.

Deviation between standard and subject values establishes the presence of a disease state. For diagnostic applications, in certain embodiments, anti-hTERT antibodies typically will be labeled with a detectable moiety. The detectable moiety can be any one which is capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin; or an enzyme, such as alkaline phosphatase, b-galactosidase, or horseradish peroxidase (Bayer et al., *Meth. Enz.*, 184: 138–163, 1990).

Pharmaceutical Compositions

Pharmaceutical compositions of telomerase selective binding agents are within the scope of the present invention. Such compositions comprise a therapeutically or prophylactically effective amount of an telomerase selective binding agent such as an antibody, or a fragment, variant, derivative or fusion thereof, in admixture with a pharmaceutically acceptable agent. In a preferred embodiment, pharmaceutical compositions comprise anti-telomerase antagonist antibodies which inhibit partially or completely at least one biological activity of telomerase in admixture with a pharmaceutically acceptable agent. Typically, the antibodies will be sufficiently purified for administration to an animal.

Pharmaceutically acceptable agents for use in the compositions of the invention include carriers, excipients, diluents, antioxidants, preservatives, coloring, flavoring and diluting agents, emulsifying agents, suspending agents, solvents, fillers, bulking agents, buffers, delivery vehicles, tonicity agents, cosolvents, wetting agents, complexing agents, buffering agents, antimicrobials and surfactants, as are well known in the art.

Neutral buffered saline or saline mixed with serum albumin are exemplary appropriate carriers. Also included in the compositions are antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol. Also by way of example, suitable tonicity enhancing agents include alkali metal halides (preferably sodium or potassium chloride), mannitol, sorbitol and the like. Suitable preservatives include, but are not limited to, benzalkonium chloride, thimerosal, phenethyl alcohol, methylparaben, propylparaben, chlorhexidine, sorbic acid and the like. Hydrogen peroxide may also be used as preservative. Suitable cosolvents are for example glycerin, propylene glycol, and polyethylene glycol. Suitable complexing agents are for example caffeine, polyvinylpyrrolidone, beta-cyclodextrin or hydroxy-propyl-beta-cyclodextrin. Suitable surfactants or wetting agents include sorbitan esters, polysorbates such as polysorbate 80, tromethamine, lecithin, cholesterol, tyloxapal and the like. The buffers can be conventional buffers such as acetate, borate, citrate, phosphate, bicarbonate, or Tris-HCl. Acetate buffer may be around pH 4.0–5.5 and Tris buffer may be around pH 7.0–8.5. Additional pharmaceutical agents are set forth in *Remington's Pharmaceutical Sciences,* 18th Edition, A. R. Gennaro, ed., Mack Publishing Company 1990, the relevant portions of which are hereby incorporated by reference.

The compositions may be in liquid form or in a lyophilized or freeze-dried form. Lypholized forms may include excipients such as sucrose. The compositions of the invention are suitable for parenteral administration. In preferred embodiments, the compositions are suitable for injection or infusion into an animal by any route available to the skilled worker, such as subcutaneous, intravenous, intramuscular, intraperitoneal, intracerebral (intraparenchymal), intracerebroventricular, intramuscular, intraocular, intraarterial, or intralesional routes. A parenteral formulation will typically be a sterile, pyrogen-free, isotonic aqueous solution, optionally containing pharmaceutically acceptable preservatives.

The optimal pharmaceutical formulation may be readily determined by one skilled in the art depending upon the intended route of administration, delivery format and desired dosage.

Other formulations are also contemplated by the invention. The pharmaceutical compositions also may include particulate preparations of polymeric compounds such as polylactic acid, polyglycolic acid, etc. or the introduction of a telomerase selective binding agent (such as an antibody) into liposomes. Hyaluronic acid may also be used, and this may have the effect of promoting sustained duration in the circulation. Pharmaceutical compositions also include the formulation of telomerase selective binding agents (such as antibodies) with an agent, such as injectable microspheres, bio-erodible particles or beads, or liposomes, that provides for the controlled or sustained release of a selective binding agent which may then be delivered as a depot injection. Other suitable means for delivery include implantable delivery devices.

A pharmaceutical composition comprising a telomerase selective binding agent (such as an antibody) may be formulated as a dry powder for inhalation. Such inhalation solutions may also be formulated in a liquefied propellant for aerosol delivery. In yet another formulation, solutions may be nebulized.

It is also contemplated that certain formulations containing telomerase selective binding agents may be administered orally. Formulations administered in this fashion may be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents may be included to facilitate absorption of a selective binding agent. Diluents, flavorings, low melting point waxes, vegetable oils, lubricants, suspending agents, tablet disintegrating agents, and binders may also be employed.

Another preparation may involve an effective quantity of an telomerase selective binding agent in a mixture with non-toxic excipients which are suitable for the manufacture of tablets. By dissolving the tablets in sterile water, or another appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional formulations will be evident to those skilled in the art, including formulations involving telomerase selective binding agents in combination with one or more other therapeutic agents. Techniques for formulating a variety of other sustained- or controlled-delivery means, such as liposome carriers, bio-erodible microparticles or porous beads and depot injections, are also known to those skilled in the art. See, for example, the Supersaxo et al. description of controlled release porous polymeric microparticles for the delivery of pharmaceutical compositions (See WO 93/15722; the disclosure of which is hereby incorporated by reference).

Regardless of the manner of administration, the specific dose may be calculated according to body weight, body surface area or organ size. Further refinement of the calculations necessary to determine the appropriate dosage for treatment involving each of the above mentioned formulations is routinely made by those of ordinary skill in the art and is within the ambit of tasks routinely performed by them. Appropriate dosages may be ascertained through use of appropriate dose-response data.

One may further administer the present pharmaceutical compositions by pulmonary administration, see, e.g., PCT WO94/20069, which discloses pulmonary delivery of chemically modified proteins, herein incorporated by reference. For pulmonary delivery, the particle size should be suitable for delivery to the distal lung. For example, the particle size may be from 1 mm to 5 mm, however, larger particles may be used, for example, if each particle is fairly porous.

Alternatively or additionally, the compositions may be administered locally via implantation into the affected area of a membrane, sponge, or other appropriate material on to which a telomerase selective binding agent has been absorbed or encapsulated. Where an implantation device is used, the device may be implanted into any suitable tissue or organ, and delivery of a telomerase selective binding agent may be directly through the device via bolus, continuous administration, or catheter using continuous infusion.

Pharmaceutical compositions of the invention may also be administered in a sustained release formulation or preparation. Suitable examples of sustained-release preparations include semipermeable polymer matrices in the form of shaped articles, e.g. films, or microcapsules. Sustained release matrices include polyesters, hydrogels, polylactides (See e.g., U.S. Pat. No. 3,773,919, EP 58,481), copolymers of L-glutamic acid and gamma ethyl-L-glutamate (Sidman et al, *Biopolymers,* 22: 547–556 [1983]), poly (2-hydroxyethyl-methacrylate) (Langer et al, *J. Biomed. Mater. Res.,* 15: 167–277 [1981] and Langer, *Chem. Tech.* 12: 98–105 [1982]), ethylene vinyl acetate, or poly-D(-)-3-hydroxybutyric acid. Sustained-release compositions also may include liposomes, which can be prepared by any of several methods known in the art. See e.g., Eppstein et al., *Proc. Natl. Acad. Sci. USA,* 82: 3688–3692 (1985); EP 36,676; EP 88,046; and EP 143,949.

hTERT selective binding agents may be employed alone or in combination with other pharmaceutical compositions. Compositions comprising separately or together a telomerase antagonist and a cancer therapy agent may be used for the treatment and/or prevention of cancer. For example, pharmaceutical compositions comprising separately or together a telomerase antagonist and either another telomerase antagonist, a matrix metalloprotease inhibitor, integrin antagonist, nonsteroidal anti-inflammatory drugs (NSAIDs), or cyclooxygenase-2 inhibitor, DNA damaging agents or other anti-cancer drug treatments (e.g. radiation) or other small molecule antagonists used for the treatment and/or prevention of cancer, Further, compositions comprising separately or together a telomerase antagonist and an AIDS therapy agent may be used for the treatment and/or prevention of cancer. Other combinations with a telomerase antagonist or agonist are possible depending upon the condition being treated.

In addition, hTERT selective binding agents may be employed to target therapeutic molecules to hyperproliferative tissues expressing hTERT. Administration of hTERT specific antibodies conjugated to radiolabels as a method of targeting low doses of radiation to hyperproliferative tissues such as tumor cells. Radiolabels that can be conjugated to hTERT specific antibodies include, but are not limited to, $^{64}$Cu, $^{67}$Cu, $^{90}$Y, $^{177}$Lu, $^{186}$Re, $^{188}$Re, $^{211}$At, $^{212}$Bi, and $^{213}$Bi. (See Buchsbaum, *Sem. Rad. Oncol.,* 10: 156–67 [2000]).

Immunotoxins can also be chemically or genetically conjugated to hTERT specific antibodies for targeting to hyperproliferative tissues. The conjugated immunotoxins also need to be modified to decrease binding to normal tissue. Immunotoxins which can be conjugated to hTERT specific antibodies include, but are not limited to, *Pseudomonas* exotoxin, Diphtheria toxin, ricin, pokeweed antiviral protein, glonin and saporin. (See Brinkman, In vivo, 14:21–28 [2000]; Frankel et al., *Clin. Canc. Res.,* 6: 326–334 [2000].

It may be desirable in some instances to use a pharmaceutical composition comprising a telomerase selective binding agent compositions in an ex vivo manner. Here, cells, tissues, or organs that have been removed from the patient are exposed to pharmaceutical compositions comprising telomerase selective binding agents after which the cells, tissues and/or organs are subsequently implanted back into the patient.

In other cases, a composition comprising a telomerase selective binding agent may be delivered through implanting into patients certain cells that have been genetically engineered, using methods such as those described herein, to express and secrete the polypeptides, selective binding agents, fragments, variants, or derivatives. Such cells may be animal or human cells, and may be derived from the patient's own tissue or from another source, either human or non-human. Optionally, the cells may be immortalized. However, in order to decrease the chance of an immunological response, it is preferred that the cells be encapsulated to avoid infiltration of surrounding tissues. The encapsulation materials are typically biocompatible, semi-permeable polymeric enclosures or membranes that allow release of the protein product(s) but prevent destruction of the cells by the patient's immune system or by other detrimental factors from the surrounding tissues.

Methods used for membrane encapsulation of cells are familiar to the skilled artisan, and preparation of encapsulated cells and their implantation in patients may be accomplished without undue experimentation. See, e.g., U.S. Pat. Nos. 4,892,538; 5,011,472; and 5,106,627. A system for encapsulating living cells is described in PCT WO 91/10425 (Aebischer et al.). Techniques for formulating a variety of other sustained or controlled delivery means, such as liposome carriers, bio-erodible particles or beads, are also known to those in the art, and are described. The cells, with or without encapsulation, may be implanted into suitable body tissues or organs of the patient.

A therapeutically or prophylactically effective amount of a pharmaceutical composition comprising a telomerase selective binding agent (such as an anti-telomerase antibody, or fragment, variant, derivative, and fusion thereof) will depend, for example, upon the therapeutic objectives such as the indication for which the composition is being used, the route of administration, and the condition of the subject. Telomerase antagonist antibodies or antigen binding domains of the invention are administered in a therapeutically or prophylactically effective amount to prevent and/or treat loss of bone associated with metastatic bone disease. A "therapeutically or prophylactically effective amount" of a telomerase antagonist antibody is that amount which reduces the rate and/or extent of telomere elongation, and subsequently cell proliferation.

Determination of telomerase activity can be accomplished through use of the telomeric repeat amplification protocol (TRAP) assay. The telomerase or unknown protein of cell extract of interest is combined with necessary reagents to facilitate telomere extension. The synthesized extension products are then uses as templates for PCR amplification (see Kim et al., *Science,* 266:2011–2015 [1994]).

The hTERT monoclonal antibodies described herein act as antagonists for telomerase activity as measured by the TRAP assay. (See FIG. 5). As described in detail in Example 9, hTERT monoclonal antibodies decreased telomerase activity in a dose dependent manner as indicated by the reduction in the amount of telomerase extension products in FIG. 5. This suggests that the binding of hTERT by the monoclonal antibodies of the invention will significantly decrease the catalytic activity of telomerase.

Target Sites for Antibody Mutagenesis

Certain strategies can be employed to manipulate inherent properties of an antibody, such as the affinity of the antibody for its target. These strategies include the use of site-specific or random mutagenesis of the DNA encoding the antibody to change the amino acids present in the protein, followed by a screening step designed to recover antibody variants that exhibit the desired change, e.g. increased or decreased affinity.

The amino acid residues most commonly targeted in mutagenic strategies are those in the complementarity-determining region (CDR) or hyper-variable region, which are a subset of amino acids that make up part of the light and the heavy variable chain segments of the antibody. These regions contain the residues which actually interact with antigen and other amino acids which affect the spatial arrangement of these residues. However, amino acids in the framework regions of the variable domains outside the CDR regions have also been shown to make substantial contributions to the antigen-binding properties of the antibody, and can be targeted to manipulate such properties See Hudson, P. J. *Curr. Opin. Biotech.*, 9: 395–402 [1999] and references therein.

Smaller and more effectively screened libraries of antibody variants could be produced by restricting random or site-directed mutagenesis to sites in the CDRs that correspond to areas prone to "hyper-mutation" during the somatic affinity maturation process. See Chowdhury, P. S. and Pastan I., *Nature Biotech.*, 17: 568–572 [1999] and references therein. The types of DNA elements known to define hypermutation sites in this manner include direct and inverted repeats, certain consensus sequences, secondary structures, and palindromes. The consensus DNA sequences include the tetrabase sequence Purine-G-Pyrimidine-A/T (i.e. A or G-G-C or T--A or T) and the serine codon AGY (wherein Y can be a C or a T).

Thus, an embodiment of the present invention is mutagenic strategies with the goal of increasing the affinity of an antibody for its target. These strategies include mutagenesis of the entire variable heavy and light chain, mutagenesis of the CDR regions only, mutagenesis of the consensus hypermutation sites within the CDRs, or any combination of these approaches ("mutagenesis" in this context could be random or site-directed).

Definitive delineation of the CDR regions and identification of residues comparing the binding site of an antibody can be accomplished though solving the structure of the antibody in question, and the antibody:ligand complex, through techniques known to those skilled in the art, such as X-ray crystallography. Various methods based on analysis and characterization of such antibody crystal structures are known to those of skill in the art and can be employed, although not definitive, to approximate the CDR regions. Examples of such commonly used methods include the Kabat, Chothia, and contact definitions.

The Kabat definition is based on the sequence variability and is the most commonly used definition to predict CDR regions. (Johnson and Wu, *Nucleic Acids Research*, 28: 214–8 [2000]). The Chothia definition is based on the location of the structural loop regions. (Chothia et al., *J. Mol. Biol.*, 196: 901–17 [1986]; Chothia et al, *Nature*, 342: 877–83 [1989]) The AbM definition is a compromise between the Kabat and Chothia definition. AbM is an integral suite of programs for antibody structure modeling produced by Oxford Molecular Group. The AbM suite models the tertiary structure of an antibody from primary sequencing using a combination of knowledge databases and ab initio methods An additional definition, known as the contact definition, has been recently introduced. (MacCallum et al., *J. Mol. Biol.*, 5:732–45 [1996]). This definition is based on an analysis of the available complex crystal structures.

By convention, the CDR regions in the heavy chain are referred to as H1, H2 and H3 and are numbered sequentially in order counting from the amino terminus to the carboxy terminus. The CDR regions in the light chain are referred to as L1, L2 and L3 and are numbered sequentially in order counting from the amino terminus to the carboxy terminus.

The CDR-H1 is approximately 10 to 12 residues in length and will start 4 positions after a Cys according to the Chothia and AbM definitions or 5 residues later according to the Kabat definition. The H1 is typically followed by a Trp, typically Trp-Val, but also Trp-Ile, or Trp-Ala. The length of H1 is approximately 10 to 12 residues according to the AbM definition while the Chothia definition excludes the last 4 residues.

The CDR-H2 typically starts 15 residues after the end of H1 according to the Kabat and AbM definition. The residues preceding H2 are typically Leu-Glu-Trp-Ile-Gly but there are a number of variations. H2 is typically followed by the amino acid sequence Lys/Arg-Leu/Ile/Val/Phe/Thr/Ala-Thr/Ser/Ile/Ala. According to the Kabat definition, the length of the H2 is approximately 16 to 19 residues where the AbM definition predicts the length to be 9 to 12 residues.

The CDR-H3 typically starts 33 residues after the end of H2 and is always preceded by the amino acid sequence Cy-XXX-XXX (typically Cys-Ala-Arg). The H3 is always followed by the amino acid sequence Trp-Gly-XXX-Gly. The length of H3 can be anywhere between 3 to 25 residues.

The CDR-L1 typically starts at approximately residue 24 and will always follow a Cys. The residue after the CDR-L1 is always a Trp and will typically begin the sequence Trp-Tyr-Gln, Trp-Leu-Gln, Trp-Phe-Gln, or Trp-Tyr-Leu. The length of CDR-L1 is approximately 10 to 17 residues. The punitive CDR-L1 for the anti-TERT antibodies of the invention follows this pattern exactly with a Cys residue followed by 15 amino acids then Trp-Tyr-Gln.

The CDR-L2 starts approximately 16 residues after the end of L1. It will generally follow Ile-Tyr, Val-Tyr, Ile-Lys or Ile-Phe. The length of CDR-L2 is approximately 7 residues.

The CDR-L3 always starts 33 residues after the end of L2 and always follows a Cys. L3 is always followed by the amino acid sequence Phe-Gly-XXX-Gly. The length of L3 is approximately 7 to 11 residues.

The following examples are intended for illustration purposes only, and should not be construed as limiting the scope of the invention in any way.

EXAMPLE 1

Immunization of BALB/c Mice

A group of 5 mice were initially immunized with the TERT peptide (SEAEVRQHREARPALLTSRLRFIPKC; SEQ ID NO: 10; denoted herein as "TP2 peptide") conjugated to keyhole-limpet hemocyanin (KHL). The TERT peptide corresponds to residues 602 to 616 of the catalytic subunit of human telomerase. The mice were bled from the tail every 10 days and the sera was diluted 1:500 in phosphate buffer saline (PBS). The response of the mouse to the antigen was measured by Western blots.

Full length hTERT was produced via in vitro translation using the Promega TNT (transcription and translation) T7 Reticulocyte Lysate System according to the manufacturer's instructions. hTERT was cloned into pCR vector as described in Harrington et al., *Genes Del.,* 11: 3109–15 [1997] and Beattie et al., *Curr Biol.* 8: 177–80 [1997] and plasmid DNA was isolated using standard techniques. Each TNT reaction contained: 1 µg of hTERT plasmid DNA mixed with 50% TNT Rabbit Reticulocyte Lysate, 1× TNT reaction buffer, 1 nM of every amino acid except methionine and leucine, 80 units of RNase inhibitor (Boehringer Mannheim), and 2 µl of TNT T7 polymerase. This reaction was incubated for 90 minutes at 30° C. A similar protocol was used to synthesize hTERT-D200, a hTERT protein with the first 200 amino acids deleted. The resulting full length human TERT and hTERT-D200 proteins were immunoprecipitated with Protein G Sepharose beads (Pharmacia) conjugated with anti-FLAG antibody.

The beads were incubated with anti-FLAG M2 antibody (Sigma, St. Louis, Mo.) diluted in CHAPS buffer (0.5% CHAPS, 10 mM TRIS, 1 mM $MgCl_2$, 0.1 NaCl, 10% glycerol, 1 mM DTT, RNase inhibitor, complete protease inhibitor; Boehringer Mannheim). The beads were washed and then subsequently incubated at 4° C. in the same buffer as the TNT reaction containing murine TERT.

After immunoprecipitation of the human TERT, the sepharose beads were washed with the aforementioned buffer and diluted in 4× SDS loading dye (See Sambrook et al., *Molecular Cloning, a Laboratory Manual* 2nd ed, Cold Spring Harbor, 1989). The immunoprecipitated hTERT protein was heated to 100° C. for 5 minutes and loaded onto a 4–12% gradient Tris-glycine gel (Novex, San Diego, Calif.). Additional lanes were loaded with 25 ng of GST protein, 25 ng of purified recombinant human TERT reverse transcriptase domain (hereinafter TERT-RT) and Broad Range Prestained SDS-PAGE Standard marker (Biorad, Hercules, Calif.). The proteins on the gel were transferred to Immobilon-P membrane (Millipore, Bedford, Mass.) via electroblotting and probed with polyclonal antisera from mice immunized as described above.

The protein signal on the membrane was detected by the ECL Western Blot protocol (Amersham-Pharmacia Biotech). Mouse no. 2 and mouse no. 4 had the best response to the antigen (i.e. their sera contained polyclonal antibodies that detected the recombinant hTERT) and were therefore selected for further boostings and preparation of hybridomas. Three days before preparation of the hybridomas, the mice were given an intravenous booster injection of 20 µg of TP2 peptide (SEQ ID NO: 10) which was conjugated with KLH and solublized in sterile PBS. To facilitate conjugation to KHL, a C-terminal cysteine was added to the TP2 peptide sequence using methods known in the art.

EXAMPLE 2

Hybridoma Production

To produce hybridomas secreting antibodies to hTERT, myeloma cells were fused with splenocytes from mice immunized with the TP2 peptide as described in Example 1. According to the method described in Kohler and Milstein (*Nature* 256: 495–497 [1975]).

Prior to fusion, the parental myeloma cell line (sp2/0, BALB/c origin; ATCC No. CRL 1581) was grown in Clonacell HY pre-fusion medium (MediumA) (StemCell Technologies, Vancouver, B.C.) for at least one week to ensure that the cells were well adapted. *The* sp2/0 myeloma cells were counted at the time of mid log phase growth and $2\times10^7$ viable cells were resuspended in 30 ml Medium A. Viability was determined by trypan blue exclusion.

To obtain the splenocytes for fusion, the immunized (mice nos. 2 and 4) were sacrificed and their spleens dissected. Initially, the sacrificed mouse's fur was washed with 95% ethanol and the chest cavity opened with sterile instruments. The lung and heart were cut first, then the blood was removed with a Pasteur pipette and dispensed into a microtainer tube. The blood was allowed to clot at room temperature for 30 minutes. The tube of blood was stored overnight at 4° C. Subsequently, the serum was collected after centrifugation for 15 minutes at 400×g. Sodium azide was added to a final concentration of 0.1%. This serum was used as a source of polyclonal antibody for positive controls.

The spleens from mice nos. 2 and 4 were removed quickly and placed in a petri dish containing 5 ml of Medium A, where they were rinsed to remove blood cells. The spleens were then transferred to a fresh petri dish containing 10 ml of Medium A. Each spleen was placed in a cell strainer and broken apart with the rubber end of a syringe. The splenocyte suspension was slowly removed with a 10 ml syringe attached to a 26½ gauge needle, placed in a 15 ml conical tube and centrifuged at 400×g for 10 minutes. The supernatant was discarded and cells were resuspended in Medium A. The cells were diluted 1:10 in 3% acetic acid, viability determined by trypan blue exclusion, and counted.

Cell suspensions of $1\times10^8$ viable spleen cells and $2\times10^7$ parental myeloma cells were combined in a 50 ml tube and centrifuged at 400×g for 10 minutes. The supernatant was discarded and the pellet washed twice with 40 ml of pre-warmed (37° C.) Clonacell-HY serum-free Fusion Medium (Medium B). The excess supernatant was removed with a Pasteur pipette to avoid dilution of PEG. Subsequently, the pellet was broken apart by gently tapping the bottom of the tube. Over a period of 1 minute, 1 ml of PEG solution (pre-warmed to 37° C.) was added to the pellet using a 1 ml pipette, while the cells were continuously stirred gently with the pipette tip. The stirring continued for 1–2 minutes. Subsequently, 1 ml of serum-free Medium B (pre-warmed to 37° C.) was added to the fusion mixture, while stirring continued for an additional minute. Over a period of 3 minutes, 3 ml of serum-free Medium B was added to the mixture, while stirring of the cells continued. Subsequently, 10 ml of serum-free Medium B was slowly added and the mixture was incubated for 5 minutes at 37° C.

After the incubation, 40 ml of Medium A was slowly added to the mixture. The cells were pelleted by centrifugation at 400×g for 7 minutes. The supernatant was discarded and the cells were washed in 40 ml of the same media to ensure that all the PEG was removed.

The cell pellet was slowly resuspended in 10 ml of Clonacell-HY Hybridoma Recovery Medium (Medium C) pre-warmed to 37° C. The cell suspension was transferred to a 250 ml tissue culture flask containing 40 ml of Medium C. The suspension was incubated for 16–24 hours at 37° C. in a 5% $CO_2$ atmosphere.

After the incubation in Medium C, the cells were centrifuged at 400×g for 10 minutes The cells were then resuspended in Clonacell-HY Selection Medium (Medium D) at 37° C. The mixture was gently stirred with a 10 ml pipette and incubated for 30 minutes at 37° C. in 5% $CO_2$ atmosphere. Subsequently, 9.5 ml of the Medium D suspension was plated in 100 mm petri plates (10 plates total). The plates were incubated at 37° C. in 5% $CO_2$ atmosphere. After 14 days, the plates were examined for the presence of colonies. The isolated colonies were removed from the plates with a pipettor and sterile 200 ml tips under a visual microscope. Each clone was placed into an individual well of a 96 well tissue culture plate containing 200 ml of Clonacell-HY growth medium (Medium E). The plates were incubated at 37° C. in 5% $CO_2$ atmosphere for 4 days without media changes.

The 4A5 and 4B5 murine hybridoma cell lines were deposited with the American Type Culture Collection (P.O Box 1549 Manassas, Va. 20108) on Aug. 22, 2000 and assigned accession nos. PTA-2412 and PTA-2411, respectively. This deposit was made in accordance with the Budapest Treaty and affords permanence of the deposit for at least 30 years or at least 5 years after the most recent request to furnish the sample. The deposit will be replaced if necessary.

EXAMPLE 3

Screening of Hybridoma Cultures

Selection of the hybridoma clones was carried out by testing the hybridoma culture supernanants for antibody production. Dot blot analysis was performed on the hybridoma supernatants, and mouse antibodies were detected with a sheep anti-mouse Ig horse radish peroxidase linked $F(ab')_2$ fragment (Amersham-Pharmacia Biotech). Four hundred clones were tested by dot blot and 104 clones tested positive.

Antibody production in these 104 clones was verified by the ability of the antibodies produced to detect the TP2 peptide on a Western blot. Human TERT was produced by the TNT reaction on rabbit reticulocyte lysates and immunoprecipitated as described in Example 1. Purified hTERT-RT (100 ng) was run on a 4–12% TRIS-glycine gradient gel (Novex) and transferred to a Immobilon-P membrane (Millipore). Broad range pre-stained protein standards (Biorad) were used as molecular weight markers. The membranes were probed with hybridoma superntants and an approximately 35 kD peptide (corresponding to hTERT-RT) was detected in the positive clones by ECL detection (Amersham-Pharmacia Biotech). The following clones tested positive: 1C12, 1D8, 1E9, 1G7, 2B7, 2C1, 4A5, 4B1, 4B5 4C10, 4E8, 4F7, and 4G8.

The positive clones were expanded into 24-well plates containing 1 ml of Medium E. On reaching confluence, the clones were further expanded into 6-well plates and then into small tissue culture flasks. All the clones were then frozen in liquid nitrogen.

Antibodies produded by the positive clones were characterized by isotype using mouse Ab Subclass Kit from BIACORE (Piscataway, N.J.) according to the manufacturer's instructions. This commercial kit identified mouse IgG subclasses: $IgG_1$ $IgG_{2a}$, $IgG_{2b}$, and $IgG_3$. Those antibodies which were not characterized by the BIACORE kit were isotyped by dot blot analysis using affinity purified HRP conjugated donkey anti-mouse IgM (μ chain specific; Jackson Immunoresearch Laboratories, West Grove, Pa.).

The positive hybridoma clones which survived were 4A5 and 4B5. These hybridomas continuously produced monoclonal antibodies which recognized recombinant hTERT on Western blots. The monoclonal antibodies were characterized as IgG2B type.

EXAMPLE 4

Cloning of Anti-TERT Immunoglobulin Heavy and Light Chain Variable Regions

A. Isolation of Total RNA

To clone the anti-TERT immunoglobulin heavy and light chain variable regions, total RNA was isolated from anti-TERT secreting hybridoma cells. Cells ($2 \times 10^7$) from two anti-TERT hybridoma cell lines, 4A5 and 4B5, were washed with 1× PBS and pelleted via centrifugation in a 12×75 mm round bottom polypropylene tube (Falcon # 2059). TRIzol™ Total RNA Isolation Reagent (Gibco BRL, Life Technologies, Cat# 15596-018) was added (8 ml) to each tube and the cells were lysed via repeated pipetting. The lysate was incubated for 5 minutes at room temperature prior to the addition of 1.6 ml (0.2× volume) of chloroform and vigorous shaking for 15 seconds. After standing 3 minutes at room temperature, the lysates were centrifuged at 9,000 rpm for 15 minutes in a 4° C. pre-chilled Beckman JA-17 rotor in order to separate the aqueous and organic phases. The top aqueous phase (~4.8 ml) was transferred into a new tube and mixed gently with 4 ml of isopropanol. After a 10 minute incubation at room temperature, the RNA was precipitated by centrifugation at 9,000 rpm in a 4° C. JA-17 rotor for 11 minutes. The RNA pellet was washed with 8 ml of ice-cold 75% ethanol and re-pelleting by centrifugation at 7,000× rpm for 7 minutes in a 4° C. JA-17 rotor. The ethanol wash was decanted and the RNA pellets were air-dried for 10 minutes. The RNA pellets were resuspended in 150 ml of diethylpyrocarbonate (DEPC)-treated $ddH_2O$ containing 1 ml of RNase Inhibitor (Catalogue No. 799017; Boehringer Mannheim/Roche) per 1 ml of DEPC treated $ddH_2O$. The pellets were resuspended by gentle pipetting and incubated for 20 minutes at 55° C. RNA samples were quantitated by measuring the $OD_{260nm}$ of diluted aliquots (1.0 $OD_{260nm}$ unit=40 mg/ml RNA).

B. Rapid Amplification of cDNA Ends

5' RACE was carried out to amplify the ends of the anti-TERT heavy and light chain variable regions. The 5' RACE System for Rapid Amplification of cDNA Ends Kit version 2.0 (Life Technologies, cat. no. 18374-058) was used according to the manufacturer's instructions. Degenerate 5' RACE oligonucleotide primers were designed to match the constant regions of two common classes of mouse immunoglobulin heavy chains (IgG1 and IgG2b) using the oligonucleotide design program Oligo version 5.1 (Molecular Biology Insights, Cascade Colo.). Primers were also designed to match the constant region of the mouse IgG kappa light chain. This is the only class of immunoglobulin light chain, so no degeneracy was needed in the primer design. The sequences of the primers are as follows:

| Name | Sequence | SEQ ID NO: |
|---|---|---|
| Heavy Chain GSP1 | 5'AGGTGCTGGAGGGGACAGTCACTGAGCTGC3' | 5 |
| Nested Heavy Chain | 5'GTCACWGTCACTGRCTCAGGGAARTAGC3' | 6 |
| | (W = A or T; R = A or G) | |

-continued

| Name | Sequence | SEQ ID NO: |
|---|---|---|
| Light Chain GSP1 | 5'GGGTGCTGCTCATGCTGTAGGTGCTGTCTTTGC3' | 7 |
| Nested Light Chain | 5'CAAGAAGCACACGACTGAGGCACCTCCAGATG3' | 8 |
| 5' Race Abridged Anchor Primer | 5'GGCCACGCGTCGACTAGTACGGGNNGGGNNGGG NNG3'<br>(N = Inosine) | 9 |

To amplify the mouse immunoglobulin heavy chain component, the reverse transcriptase reaction was carried in a 0.2 ml thin-walled PCR tube containing 2.5 pmoles of heavy chain GSP1 primer (SEQ ID NO: 5), 4 µg of total RNA isolated from either hybridoma clone 4A5 or 4B5, and 12 µl of DEPC treated ddH$_2$O. Likewise, for the mouse light chain component the reverse transcriptase reaction was carried out in a 0.2 ml thin-walled PCR tube containing 2.5 pmoles of light chain GSP1 primer (SEQ ID NO: 7), 4 µg of total RNA from either hybridoma clone 4A5 or 4B5, and 12 µl of DEPC treated ddH$_2$O.

The reactions were carried out in a PTC-100 programmable thermal cycler (MJ research Inc., Waltham, Mass.). The mixture was incubated at 70° C. for 10 minutes to denature the RNA and then chilled on wet ice for 1 minute. The tubes were centrifuged briefly in order to collect moisture from the lids of the tubes. Subsequently, the following components were added to the reaction: 2.5 ml of 10× PCR buffer (200 mM TRIS-HCl, pH 8.4, 500 mM KCl), 2.5 ml of 25 mM MgCl$_2$, 1 ml of 10 mM dNTP mix, and 2.5 ml of 0.1 M DTT. After mixing each tube by gentle pipetting, the tubes were placed in a PTC-100 thermocycler at 42° C. for 1 minute to pre-warm the mix. Subsequently, 1 ml (200 units) of SuperScript™ II Reverse Transcriptase (Gibco-BRL; cat no. 18089-011) was added to each tube, gently mixed by pipetting, and incubated for 45 minutes at 42° C. The reactions were cycled to 70° C. for 15 minutes to terminate the reaction, and then cycled to 37° C. RNase mix (1 µl) was then added to each reaction tube, gently mixed, and incubated at 37° C. for 30 minutes.

The first strand cDNA generated by the reverse transcriptase reaction was purified with the GlassMAX DNA Isolation Spin Cartridge (Gibco-BRL) according to the manufacturer's instructions. To each first strand reaction, 120 ml of 6M NaI binding solution was added. The cDNA/NaI solution was then transferred into a GlassMAX spin cartridge and centrifuged for 20 seconds at 13,000×g. The cartridge inserts were carefully removed and the flow-through was discarded from the tubes. The spin cartridges were then placed back into the empty tubes and 0.4 ml of cold (4° C.) 1× wash buffer was added to each spin cartridge. The tubes were centrifuged at 13,000×g for 20 seconds and the flow-through was discarded. This wash step was repeated three additional times. The GlassMAX cartridges were then washed 4 times with 0.4 ml of cold (4° C.) 70% ethanol. After the flow-through from the final 70% ethanol wash was discarded, the cartridges were placed back in the tubes and centrifuged at 13,000×g for an additional 1 minute in order to completely dry the cartridges. The spin cartridge inserts were then transferred to a fresh sample recovery tube where 50 ml of 65° C. (pre-heated) DEPC treated ddH$_2$O was quickly added to each spin cartridge. The cartridges were centrifuged at 13,000×g for 30 seconds to elute the cDNA.

C. Terminal Deoxynucleotidyl Transferase (TdT) Tailing

For each first-strand cDNA sample, the following components were added to a 0.2 ml thin-walled PCR tube: 6.5 ml of DEPC-treated ddH$_2$O, 5.0 ml of 5× tailing buffer, 2.5 ml of 2 mM dCTP, and 10 ml of the appropriate GlassMAX purified cDNA sample. Each 24 ml reaction was incubated for 2 to 3 minutes in a thermal cycler at 94° C. to denature the DNA, and chilled on wet ice for 1 minute. The contents of the tube were collected by brief centrifugation. Subsequently, 1 ml of terminal deoxynucleotidyl transferase (TdT) was added to each tube. The tubes were mixed via gentle pipetting and incubated for 10 minutes at 37° C. in a PTC-100 thermal cycler. Following this 10 minute incubation, the TdT was heat inactivated by cycling to 65° C. for 10 minutes. The reactions were cooled on ice and the TdT-tailed first-strand cDNA was stored at −20° C.

D. PCR of dC-Tailed First-Strand cDNA

Duplicate PCR amplifications (two independent PCR reactions for each dC-tailed first-strand cDNA sample) were performed in a 50 ml volume containing 200 mM dNTPs, 0.4 mM of 5' RACE Abridged Anchor Primer (SEQ ID NO: 9), and 0.4 mM of either Nested Heavy Chain GSP2 (SEQ ID NO: 6) or Nested Light Chain GSP2 (SEQ ID NO: 8), 10 mM Tris-HCl (pH 8.3), 1.5 mM MgCl$_2$, 50 mM KCl, 5 ml of dC-tailed cDNA, and 5 units of Expand™ Hi-Fi DNA polymerase (Roche/Boehringer Mannheim GmbH, Germany). The PCR reactions were amplified using a "Touchdown/Touch-up" annealing temperature protocol in a PTC-100 programmable thermal cycler (MJ Research Inc.) with the following conditions: initial denaturation of 95° C. for 40 seconds, 5 cycles at 94° C. for 20 seconds, 61° C.−2° C./cycle for 20 seconds, 72° C. for 40 seconds+1 second/cycle, followed by 5 cycles at 94° C. for 25 seconds, 53° C.+1° C./cycle for 20 seconds, 72° C. for 46 seconds+1 second/cycle, followed by 20 cycles at 94° C. for 25 seconds, 55° C. for 20 seconds, 72° C. for 51 seconds+1 second/cycle, and a final incubation of 72° C. for 5 minutes.

E. TOPO TA-Cloning

The resulting PCR products were then gel purified from a 1.0% agarose gel using the QIAQuick Gel purification system (QIAGEN Inc., Chatsworth, Calif.), TA-cloned into pCR2.1 using the TOPO TA Cloning® kit (Invitrogen, San Diego, Calif., cat. no. K4550-40), and transformed into *E. coli* TOP10F' cells (Invitrogen). Clones with inserts were identified by blue/white selection according to the manufacturer's instructions where white clones were considered positive. Cultures of 3.5 ml liquid Luria Broth (LB) containing 50 mg/ml ampicillin were innoculated with white colonies and grown at 37° C. overnight (~16 hours) with shaking at 225 rpm.

The QIAGEN Plasmid Miniprep Kit (QIAGEN Inc., cat. no. 12125) was used to purify plasmid DNA from the cultures according to the manufacturer's instructions. The plasmid DNA was suspended in 34 ml of 1× TE buffer (pH 8.0) and then sent to Amgen (Thousand Oaks, Calif.) for fluorescent dideoxy-nucleotide sequencing and automated detection (ABI/Perkin Elmer, Foster City, Calif.) with T7 (5'GTAATACGACTCACTATAGG3'; 11) and M13 Reverse (5'CAGGAAACAGCTATGACC3'; SEQ ID NO: 12) primers using standard sequencing methods. Sequencing revealed that the clones corresponded to mouse IgG sequences. Both hybridoma cell lines 4A5 and 4B5 had identical IgG heavy chain and light chain variable region sequences.

The nucleotide sequence of hTERT IgG heavy chain variable region is set forth as SEQ ID NO: 1 and is 564 nucleotides in length which encodes a 188 amino acid polypeptide (SEQ ID NO: 2). The heavy chain polypeptide has a 28 amino acid leader sequence and a 120 amino acid variable region spanning residues 29 to 148.

The nucleotide sequence of hTERT IgG light chain variable region is set forth as SEQ ID NO: 3 and is 480 nucleotides in length which encodes a 160 amino acid polypeptide (SEQ ID NO: 4). The light chain polypeptide contains a 20 amino acid leader sequence and a 110 amino acid variable region spanning residues 21 to 130. Specific residues that differ between the derived heavy chain variable regions may indicate antibody specificity.

EXAMPLE 5

Binding of Monoclonal Antibodies to hTERT

A. Western Blot Verification

Western blot analysis confirmed the monoclonal antibody produced by hybridomas 4A5 and 4B5 were specific for the human catalytic domain of human telomerase. hTERT-D200 was produced by TNT reaction on rabbit reticulocyte lysate and immunoprecipitated as described above in Example 1. As shown in FIG. 1, on 4–12% TRIS-glycine gradient gels were loaded various concentrations of recombinant TP2-Rt domain (10 ng, 50 ng, and 100 ng) and immunoprecipitated f hTERT-D200 isolated from rabbit reticulocyte lysates (2 µl, 8 µl, and 20 µl). Broad Range Prestained SDS-Page Standards (Biorad) were run as molecular weight markers. The proteins were transferred to Immobilon-P membrane (Millipore) by electroblotting and were detected with various antibodies as indicated in FIG. 1. The antibody binding was detected with the ECL detection method (Amersham-Pharmacia Biotech) and exposed for several minutes unless otherwise indicated.

FIG. 1 demonstrates the specific binding of monoclonal antibodies 4A5 (Blot C) and 4B5 (Blot D) to hTERT on a Western blot. The blots were probed with 0.2 µg/ml of either monoclonal antibody. The 35 kD hTERT recombinant fusion protein was detected by both monoclonal antibodies in the rabbit reticulocyte lysates as indicated by the lower arrow. The upper arrow indicates the specific binding of the monoclonal antibodies to the 116 deletion derivative of hTERT (i.e. hTERT-D200). The 45A and 4B5 monoclonal antibodies were less sensitive than anti-TP2 peptide antibody and therefore the blots in panals C and D (FIG. 1) were exposed in ECL reagent for 1 hour. The 4G6 clone, which produced antibodies that did not bind hTERT, were used as a negative control.

Polyclonal antibodies were generated by injecting rabbits with the recombinant fragment of hTERT reverse transcriptase domain (SEQ ID NO: 13) and denoted herein as "RT". Polyclonal antibodies were also generated by injecting rabbits with the TP2 peptide (SEQ ID NO: 10) which was used to generate the hybridomas in Example 2.

The antibodies generated with the TP2 peptide (described in Harrington et al., Genes and Dev., 11: 3109–15 [1997]) are denoted herein as "peptide". The RT and peptide polyclonal antibodies were used as positive controls for verifying that 4A5 and 4B5 monoclonal antibodies specifically detected hTERT via Western blot analysis. The RT antibody (Blot A) and the peptide antibody (Blot B) detected both the 35 kD TP2 peptide and the 116 kD deleted derivative of hTERT as indicated by the arrows on FIG. 1. The peptide antibody was very sensitive and therefore was only exposed in the ECL reagent for 1 minute.

As a negative control, Western blots were probed with a commercially available anti-GST antibody (Upstate Biotechnology, Lake Placid, N.Y.). In addition, the hybridoma clone 4G6 was also used as a negative control since this clone was determined to produce non-hTERT reactive IgM antibodies. As shown in FIG. 1, these 2 antibodies did not bind to the 35 kD or 116 kD hTERT proteins.

B. Immunoprecipitation Verification

Immunoprecipitation experiments were also carried out to verify the specificity of the 4A5 and 4B5 monoclonal antibodies. Protein G Sepharose beads (Pharmacia) were incubated with anti-mouse IgG (Amersham Biotech) in CHAPS buffer (0.5% CHAPS, 10 mM TRIS, 1 mM NaCl, 10% glycerol, 1 mM DTT, RNase inhibitor, Complete Protease Inhibitor; Boehringer Mannheim) at room temperature for 1 to 4 hours. The beads were washed and then incubated again at room temperature for 1 to 4 hours with 2 µg of one of the following antibodies: anti-GST, peptide polyclonal antibody, RT polyclonal antibody, 4A5 monoclonal antibody, 4B5 monoclonal antibody. For the negative control 4G6 antibody, the beads were incubated with 4G6 antibody in CHAPS buffer.

Following the incubation, the beads were washed with the aforementioned buffer and then incubated in the aforementioned buffer containing either 50 µl of hTERT-s200 generated by the TNT reaction on rabbit reticulocyte (see upper panels in FIG. 2) or 100 µl of 293T lysate (see lower panel in FIG. 2) for 1 to 4 hours at 4° C. The beads were washed again in the aforementioned buffer, the excess buffer removed form the beads and suspended in 4× SDS loading dye (see Sambrook et al, supra.). The samples were heated to 100° C. for 5 minutes and then loaded onto a 4–12% TRIS-gradient gel (Novex). Western blotting was carried out as described above and probed with 0.28 µg/ml of peptide polyclonal hTERT antibody and binding was detected with the ECL method.

Figure 2:
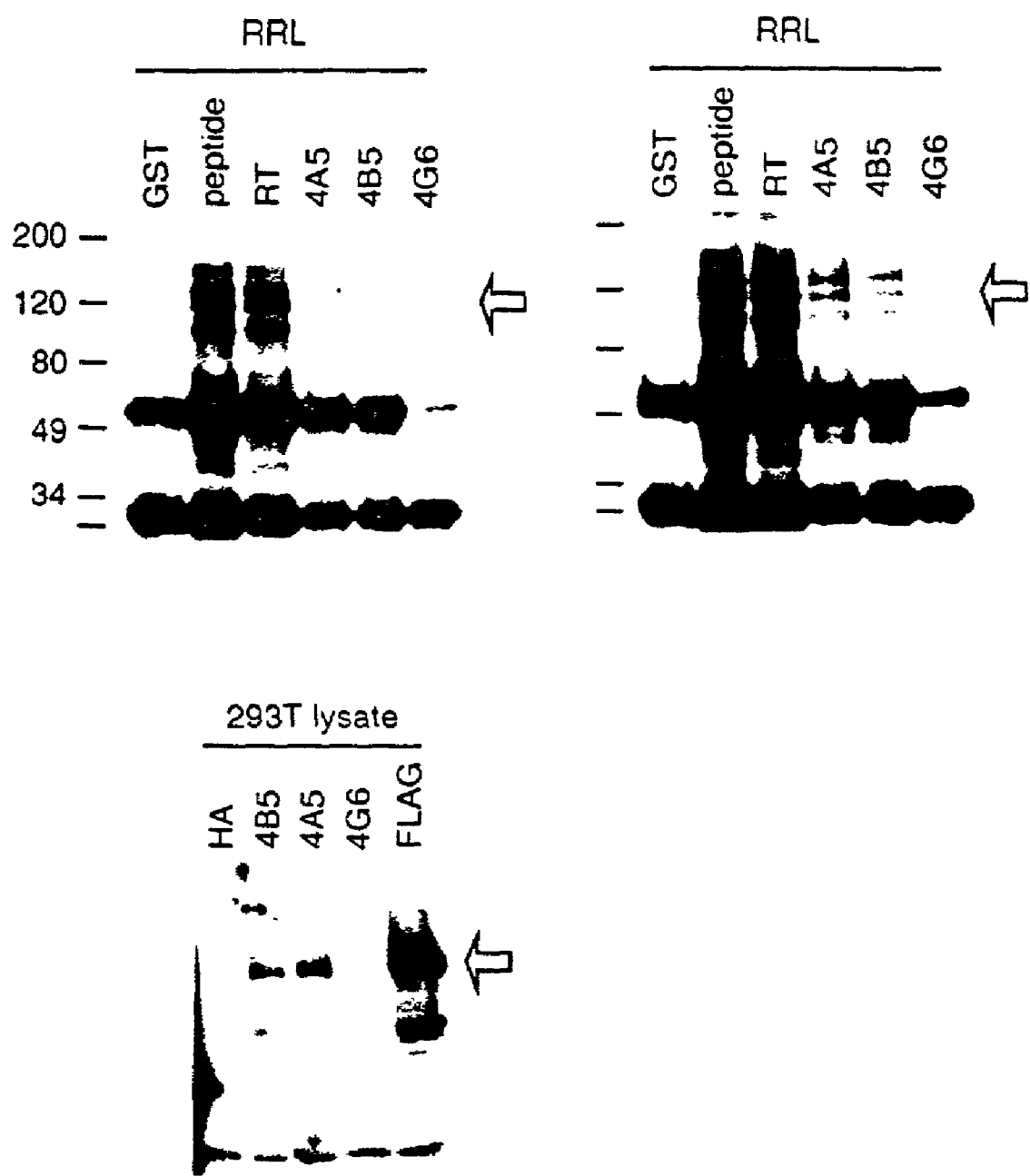
FIG. 2 depicts immunoprecipitation performed to verify the specificity of the 4A5 and 4B5 monoclonal antibodies.

As demonstrated in FIG. 2, the 4A5 and 4B5 monoclonal antibodies immunoprecipitated the 116 kD hTERT deletion derivative in rabbit reticulocyte lysates, as indicated by the arrow. The upper panel are the same blots which were exposed in ECL reagent for different periods of time. The left panel clearly indicates that the monoclonal antibodies immunoprecipitated hTERT. The lower panel demonstrates the 4A5 and 4B5 monoclonal antibodies can immunoprecipitate hTERT from 293T cells (Invitrogen) transfected with a flag-tagged hTERT protein.

The peptide and RT polyclonal antibodies were used as positive controls, which immunoprecipitated the 116 kD hTERT deletion derivative which is clearly shown in the left upper panel. The anti-GST and 4G6 antibodies were used as negative controls and did not immunoprecipitate the hTERT protein. In addition, anti-Flag and anti-Ha antibodies were used as positive and negative controls (respectively) for the 293T lysates.

These results along with the Western blot verification demonstrated that the monoclonal antibodies 4A5 and 4B5 specifically bind hTERT.

EXAMPLE 6

Inhibition of Telomerase Activity in Hela Cells

The telomerase repeat amplification (TRAP) assay was used to demonstrate telomerase inhibition by the hTERT monoclonal antibodies (Kim et al., *Science* 266: 2011–15 [1994]). Hela cell extracts (0.7 μg) were incubated in 26 μl of Hypo-buffer and various concentrations (0 μg, 0.04 μg, 0.2 μg, 1 μg or 2 μg) of the following antibodies GST, 4A5 mAb, 4B5 mAb, Peptide and RT at 4° C. for 1 hour. An aliquot of each sample (0.2 μl) was used in a standard TRAPeze reaction (Intergen, Purchase, N.Y.) according to the manufacturer's instructions. Briefly, 2 μl of each sample was incubated for 30 minutes at room temperature in 20 mM Tris-HCl (pH 8.3), 1.5 mM $MgCl_2$, 63 mM KCl, 0.05% Tween 20, 1 mM EGTA, 0.05 mM of each dATP, dTTP, dGTP, and dCTP with substrate oligonucleotide (5'AATC-CGTCGAGCAGAGGTT3'; SEQ ID NO: 14) and 2 units of Taq DNA polymerase (Gibco-BRL). Subsequently, 1 μl of $\alpha$-$^{32}$P-GTP and 1 μl of primer mix were added and PCR was carried out for 22 cycles at 94° C. for 30 seconds and 50° C. for 30 seconds, and a final incubation at 72° C. for 90 seconds. Reaction products were run on a 12% acrylamide sequencing-size gel and visualized using a Phosphoimager (Molecular Dynamics).

The monoclonal antibodies produced by hybridoma clones 4A5 and 4B5 inhibited telomerase activity. As demonstrated in FIG. 3, the 4A5 and 4B5 mAb caused a dose dependent decrease in telomerase extension products. This DNA laddering is a hallmark of telomerase catalytic activity demonstrating the addition of telomeric repeats to the substrate oligonucleotide. The GST and 4G6 antibodies were used as negative controls. These control antibodies did not specifically inhibit telomerase catalytic activity. The inhibition at high antibody concentrations is non-specific.

EXAMPLE 7

Prediction of CDR regions of the Telomerase Monoclonal Antibodies

The complementarity-determining (CDR) regions of the TERT-neutralizing monoclonal antibodies were predicted according to the following definitions: Kabat, Chothia, AbM, and the contact definition. These regions are underlined in FIGS. 4*a* and 4*b* (heavy and light chains, respectively). The areas conforming to the consensus sequence for hyper-mutations are bold. The CDRs in the heavy chain denoted H1, H2 and H3 span residues 54 to 63, 78 to 93, and 126 to 137 of SEQ ID NO: 2, respectively. The CDRs in the light chain denoted as L1, L2 and L3 span residues 44 to 58, 74 to 80, and 113 to 121 of SEQ ID NO: 4, respectively.

The invention claimed is:

1. A hybridoma deposited at the American Type Culture Collection identified by accession number PTA-2412.

2. A hybridoma deposited at American Type Culture Collection identified by accession number PTA-2411.

3. An isolated antibody or antibody fragment comprising the antigen-binding domain of a monoclonal antibody produced by the hybridoma of claim 1 or 2, wherein the antibody or antibody fragment binds to the catalytic subunit of human telomerase.

4. An isolated antibody fragment according to claim 3 which is a scFv.

5. The isolated antibody according to claim 3 which is in the form of a whole antibody.

6. The isolated antibody fragment according to claim 3 which further comprises a human Fc domain.

7. The isolated antibody or fragment according to claim 3 that is a humanized antibody.

8. An isolated and purified antibody or antibody fragment comprising an antibody heavy chain variable region having the amino acid sequence encoded by the polynucleotide sequence of SEQ ID NO: 1, and an antibody light chain variable region having the amino acid sequence encoded by the polynucleotide sequence of SEQ ID NO: 3, wherein the antibody or antibody fragment binds to the catalytic subunit of human telomerase.

9. An antibody or antibody fragment according to claim 3 comprising a heavy chain having the amino acid sequence of SEQ ID NO: 2 and a light chain having the amino acid sequence of SEQ ID NO: 4.

10. An antibody or antibody fragment thereof according to claim 3 wherein the heavy chain variable region comprises the amino acid sequence set forth in SEQ ID NO: 2.

11. An antibody or antibody fragment thereof according to claim 3 wherein the light chain variable region comprises the amino acid sequence set forth in SEQ ID NO: 4.

12. An antibody or antibody fragment of claim 9 which is a humanized antibody.

13. An antibody or antibody fragment of claim 9 which is a CDR grafted antibody.

14. An antibody or antibody fragment according to any one of claims 1, 4, 5, 6, 7, 8, 9–11 or 12–13 that inhibits telomerase activity.

15. A composition comprising an isolated monoclonal antibody or antibody fragment thereof comprising the antigen-binding domain of the monoclonal antibody produced by the hybridoma of claim 1 or 2, wherein the antigen binding domain binds the catalytic subunit of human telomerase, and a carrier.

16. The composition according to claim 15 wherein the antibody or antibody fragment thereof inhibits telomerase activity.

17. A composition comprising an isolated antibody or antibody fragment thereof comprising the antigen-binding domain of the antibody comprising the amino acid sequence set forth in SEQ ID NOS: 2 and 4, wherein the antigen binding domain binds the catalytic subunit of human telomerase, and a carrier.

18. An antibody or antibody fragment thereof according to claim 3 that inhibits telomerase activity.

19. A composition according to claim 17 wherein the antibody or antibody fragment thereof inhibits telomerase activity.

* * * * *

UNITED STATES PATENT AND TRADEMARK OFFICE
CERTIFICATE OF CORRECTION

PATENT NO. : 7,078,491 B1
APPLICATION NO. : 09/957157
DATED : July 18, 2006
INVENTOR(S) : Lea A. Harrington It is certified that error appears in the above-identified patent and that said Letters Patent is hereby corrected as shown below:

In the Specification:
At Column 9, line 29 please delete "myxosareoma" and insert --myxosarcoma--
At Column 12, line 2 please delete "legion" and insert --region--
At Column 17, line 57 please insert --$^{131}$I-- immediately before "$^{177}$Lu"
At Column 24, line 5 please delete "type" and insert --isotype--
At Column 40, line 41 please delete "1" immediately before "4, 5, 6, 7, 9-11 or 12-13"

Figure 3:
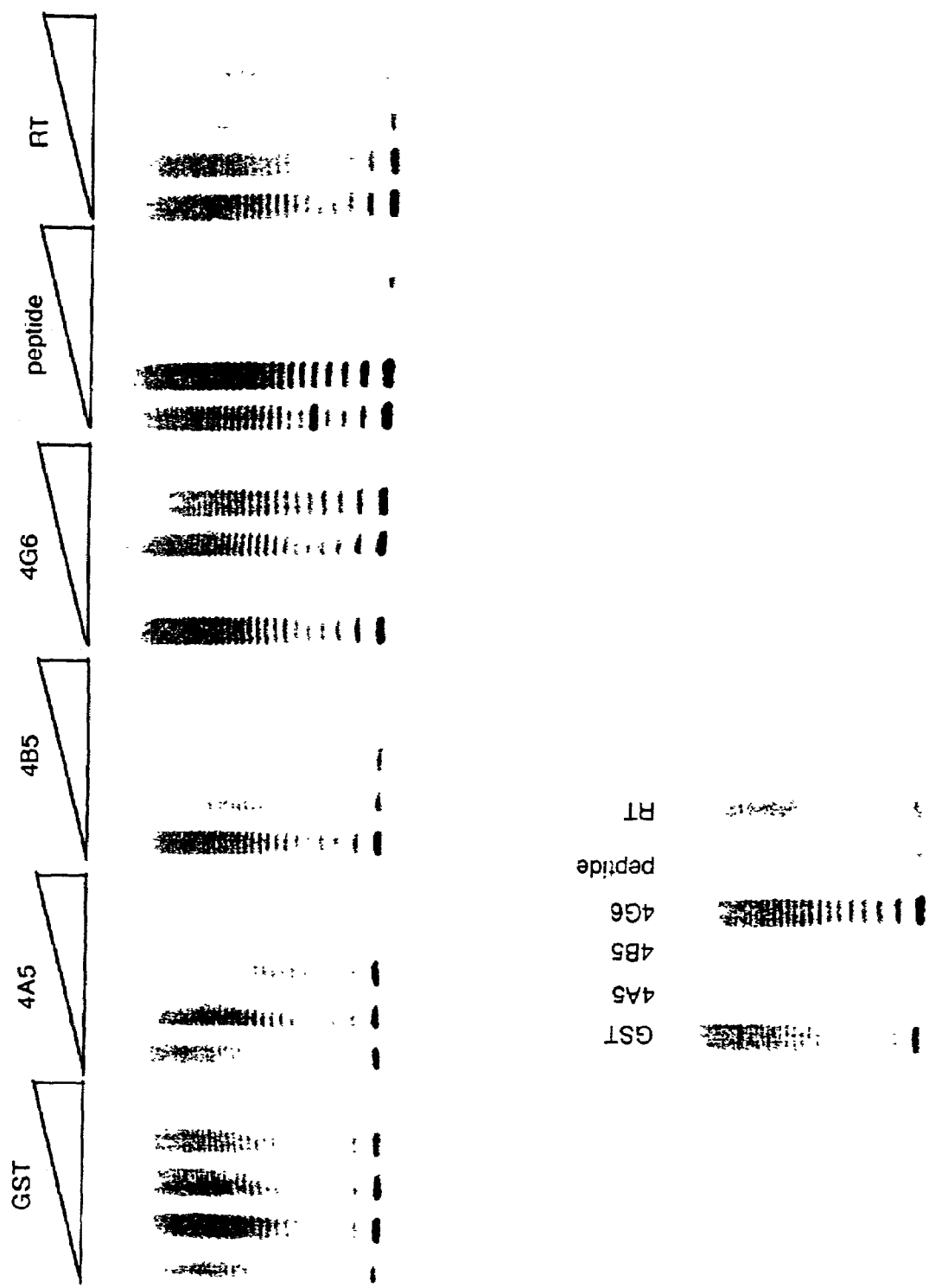
FIG. 3 depicts inhibition of telomerase activity in Hela cell extracts by hTERT antibodies.
Figure 3:
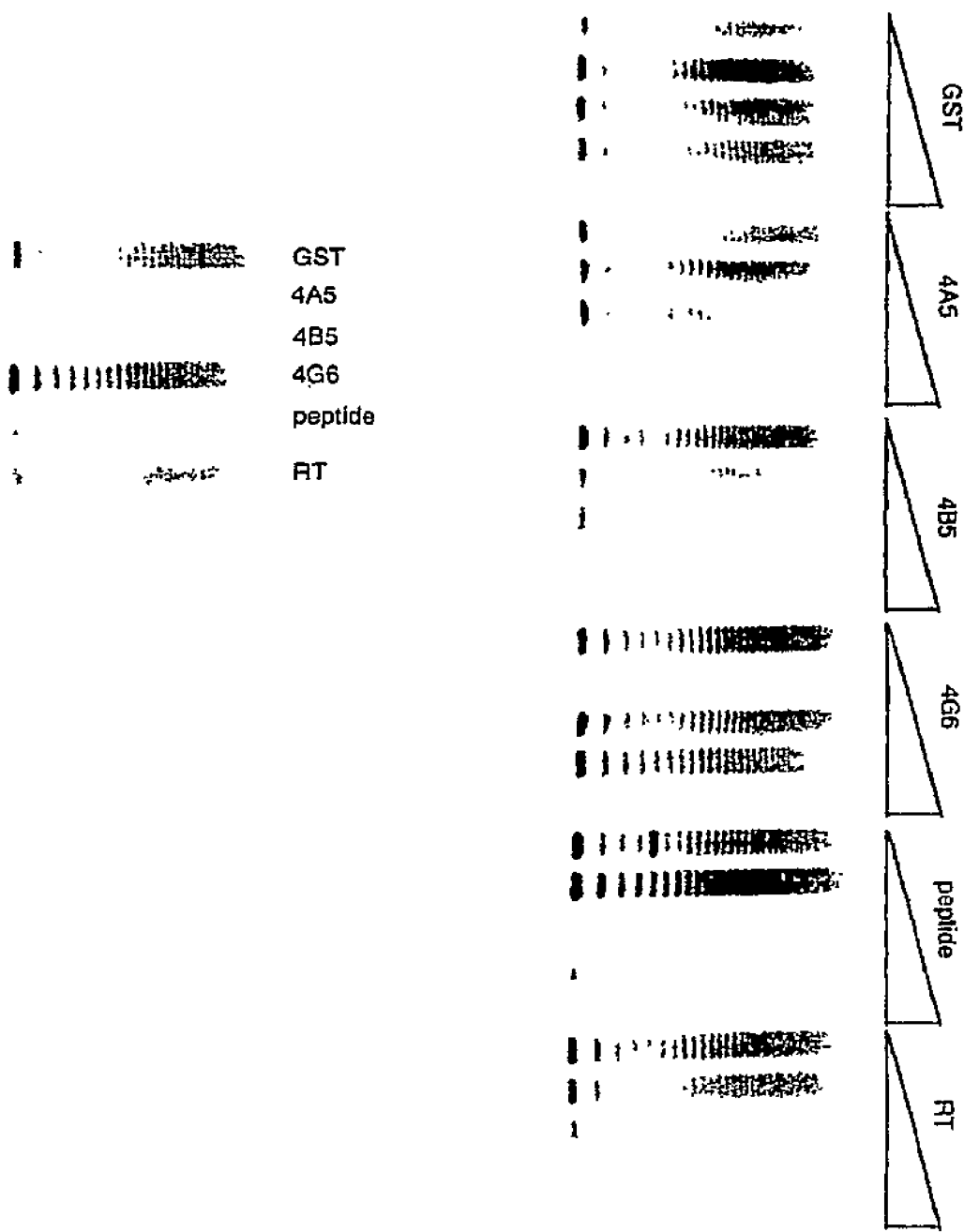

In the Figures:

Figure 3 is upside down. (see attached)

Signed and Sealed this

Second Day of January, 2007

JON W. DUDAS
*Director of the United States Patent and Trademark Office*

SEQUENCE LISTING

```
<160> NUMBER OF SEQ ID NOS: 14

<210> SEQ ID NO 1
<211> LENGTH: 564
<212> TYPE: DNA
<213> ORGANISM: Homo sapiens
<220> FEATURE:
<221> NAME/KEY: CDS
<222> LOCATION: (1)..(564)

<400> SEQUENCE: 1 atg agc act gaa cac aga cac ctc acc atg aac ttc ggg ttc agg ttg      48
Met Ser Thr Glu His Arg His Leu Thr Met Asn Phe Gly Phe Arg Leu
  1               5                  10                  15 att ttc ctt gtc ctt gtt tta aaa ggt gtc cag tgt gaa gtg aag ctg      96
Ile Phe Leu Val Leu Val Leu Lys Gly Val Gln Cys Glu Val Lys Leu
             20                  25                  30 gtg gag tct ggg gga ggc tta gtg aag cct gga ggg tcc ctg aaa ctc     144
Val Glu Ser Gly Gly Gly Leu Val Lys Pro Gly Gly Ser Leu Lys Leu
         35                  40                  45 tcc tgt gca gcc tct gga ttc act ttc agt agc tat gcc atg tct tgg     192
Ser Cys Ala Ala Ser Gly Phe Thr Phe Ser Ser Tyr Ala Met Ser Trp
     50                  55                  60 gtt cgc cag act cca gag aag agg ctg gag tgg gtc gca tcc att agt     240
Val Arg Gln Thr Pro Glu Lys Arg Leu Glu Trp Val Ala Ser Ile Ser
 65                  70                  75                  80 agt ggt ggt aac acc tac tat cca gac aat gtg cag ggc cga ttc acc     288
Ser Gly Gly Asn Thr Tyr Tyr Pro Asp Asn Val Gln Gly Arg Phe Thr
                 85                  90                  95 atc tcc aga gat aat gcc agg aac atc ctc tac ctt caa atg agc agt     336
Ile Ser Arg Asp Asn Ala Arg Asn Ile Leu Tyr Leu Gln Met Ser Ser
```

-continued

```
                    100                 105                 110
ctg agg tct gag gac acg gcc atg ttt tac tgt gcg aga gag ggg gtc         384
Leu Arg Ser Glu Asp Thr Ala Met Phe Tyr Cys Ala Arg Glu Gly Val
            115                 120                 125 tat gat acc tac gga ggg gtt gac tac tgg ggc caa ggc acc act ctc         432
Tyr Asp Thr Tyr Gly Gly Val Asp Tyr Trp Gly Gln Gly Thr Thr Leu
        130                 135                 140 aca gtc tcc tca gcc aaa aca aca ccc cca tca gtc tat cca ctg gcc         480
Thr Val Ser Ser Ala Lys Thr Thr Pro Pro Ser Val Tyr Pro Leu Ala
145                 150                 155                 160 cct ggg tgt gga gat aca act ggt tcc tcc gtg act ctg gga tgc ctg         528
Pro Gly Cys Gly Asp Thr Thr Gly Ser Ser Val Thr Leu Gly Cys Leu
                165                 170                 175 gtc aag ggc tat ttc cct gag tca gtg aca gtg aca                         564
Val Lys Gly Tyr Phe Pro Glu Ser Val Thr Val Thr
        180                 185
```

<210> SEQ ID NO 2
<211> LENGTH: 188
<212> TYPE: PRT
<213> ORGANISM: Homo sapiens

<400> SEQUENCE: 2

```
Met Ser Thr Glu His Arg His Leu Thr Met Asn Phe Gly Phe Arg Leu
  1               5                  10                  15

Ile Phe Leu Val Leu Val Leu Lys Gly Val Gln Cys Glu Val Lys Leu
                20                  25                  30

Val Glu Ser Gly Gly Gly Leu Val Lys Pro Gly Gly Ser Leu Lys Leu
            35                  40                  45

Ser Cys Ala Ala Ser Gly Phe Thr Phe Ser Ser Tyr Ala Met Ser Trp
    50                  55                  60

Val Arg Gln Thr Pro Glu Lys Arg Leu Glu Trp Val Ala Ser Ile Ser
 65                  70                  75                  80

Ser Gly Gly Asn Thr Tyr Tyr Pro Asp Asn Val Gln Gly Arg Phe Thr
                85                  90                  95

Ile Ser Arg Asp Asn Ala Arg Asn Ile Leu Tyr Leu Gln Met Ser Ser
            100                 105                 110

Leu Arg Ser Glu Asp Thr Ala Met Phe Tyr Cys Ala Arg Glu Gly Val
        115                 120                 125

Tyr Asp Thr Tyr Gly Gly Val Asp Tyr Trp Gly Gln Gly Thr Thr Leu
    130                 135                 140

Thr Val Ser Ser Ala Lys Thr Thr Pro Pro Ser Val Tyr Pro Leu Ala
145                 150                 155                 160

Pro Gly Cys Gly Asp Thr Thr Gly Ser Ser Val Thr Leu Gly Cys Leu
                165                 170                 175

Val Lys Gly Tyr Phe Pro Glu Ser Val Thr Val Thr
            180                 185     188
```

<210> SEQ ID NO 3
<211> LENGTH: 480
<212> TYPE: DNA
<213> ORGANISM: Homo sapiens
<220> FEATURE:
<221> NAME/KEY: CDS
<222> LOCATION: (1)..(480)

<400> SEQUENCE: 3

```
atg gag aca gac aca atc ctg cta tgg gtg ctg ctg ctc tgg gtt cca         48
Met Glu Thr Asp Thr Ile Leu Leu Trp Val Leu Leu Leu Trp Val Pro
```

-continued

```
          1               5                   10                  15
ggc tcc act ggt gac att gtg ttg acc caa tct cca act tct ttg gct     96
Gly Ser Thr Gly Asp Ile Val Leu Thr Gln Ser Pro Thr Ser Leu Ala
                    20                  25                  30 gtg tct cta ggg cag agg gcc acc atc tcc tgc aag gcc agc caa agt    144
Val Ser Leu Gly Gln Arg Ala Thr Ile Ser Cys Lys Ala Ser Gln Ser
            35                  40                  45 gtt gat tat gat ggt gat agt ttt ata aac tgg tat caa cag aca cca    192
Val Asp Tyr Asp Gly Asp Ser Phe Ile Asn Trp Tyr Gln Gln Thr Pro
    50                  55                  60 gga cag cct ccc aaa ctc ctc atc tat gct gca tcc aat ctt gca tct    240
Gly Gln Pro Pro Lys Leu Leu Ile Tyr Ala Ala Ser Asn Leu Ala Ser
65                  70                  75                  80 ggg atc cca gcc agg ttt agt ggc agt ggg tct ggg aca gac ttc acc    288
Gly Ile Pro Ala Arg Phe Ser Gly Ser Gly Ser Gly Thr Asp Phe Thr
                    85                  90                  95 ctc aac atc cat cct gtg gag gag gag gat gct gca acc tat tac tgt    336
Leu Asn Ile His Pro Val Glu Glu Glu Asp Ala Ala Thr Tyr Tyr Cys
            100                 105                 110 cag caa agt aat gag gct cct ccg acg ttc ggt ggc ggc acc aaa ctg    384
Gln Gln Ser Asn Glu Ala Pro Pro Thr Phe Gly Gly Gly Thr Lys Leu
    115                 120                 125 gaa atc aaa cgg gct gat gct gca cca act gta tcc atc ttc cca cca    432
Glu Ile Lys Arg Ala Asp Ala Ala Pro Thr Val Ser Ile Phe Pro Pro
130                 135                 140 tcc agt gag cag tta aca tct gga ggt gcc tca gtc gtg tgc ttc ttg    480
Ser Ser Glu Gln Leu Thr Ser Gly Gly Ala Ser Val Val Cys Phe Leu
145                 150                 155                 160
```

<210> SEQ ID NO 4
<211> LENGTH: 160
<212> TYPE: PRT
<213> ORGANISM: Homo sapiens

<400> SEQUENCE: 4

```
Met Glu Thr Asp Thr Ile Leu Leu Trp Val Leu Leu Leu Trp Val Pro
 1               5                   10                  15

Gly Ser Thr Gly Asp Ile Val Leu Thr Gln Ser Pro Thr Ser Leu Ala
                    20                  25                  30

Val Ser Leu Gly Gln Arg Ala Thr Ile Ser Cys Lys Ala Ser Gln Ser
            35                  40                  45

Val Asp Tyr Asp Gly Asp Ser Phe Ile Asn Trp Tyr Gln Gln Thr Pro
    50                  55                  60

Gly Gln Pro Pro Lys Leu Leu Ile Tyr Ala Ala Ser Asn Leu Ala Ser
65                  70                  75                  80

Gly Ile Pro Ala Arg Phe Ser Gly Ser Gly Ser Gly Thr Asp Phe Thr
                    85                  90                  95

Leu Asn Ile His Pro Val Glu Glu Glu Asp Ala Ala Thr Tyr Tyr Cys
            100                 105                 110

Gln Gln Ser Asn Glu Ala Pro Pro Thr Phe Gly Gly Gly Thr Lys Leu
    115                 120                 125

Glu Ile Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160
```

<210> SEQ ID NO 5
<211> LENGTH: 30

```
<212> TYPE: DNA
<213> ORGANISM: Artificial Sequence
<220> FEATURE:
<223> OTHER INFORMATION: Description of Artificial Sequence: Primer

<400> SEQUENCE: 5
aggtgctgga ggggacagtc actgagctgc                                      30

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Primer
<221> NAME/KEY: misc_feature
<222> LOCATION: (6)
<223> OTHER INFORMATION: W = A or T
<221> NAME/KEY: misc_feature
<222> LOCATION: (14)
<223> OTHER INFORMATION: R = A or G
<221> NAME/KEY: misc_feature
<222> LOCATION: (23)
<223> OTHER INFORMATION: R = A or G

<400> SEQUENCE: 6
gtcacwgtca ctgrctcggg aartagc                                         27

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 7
gggtgctgct catgctgtag gtgctgtctt tgc                                  33

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 8
caagaagcac acgactgagg cacctccaga tg                                   32

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Primer
<221> NAME/KEY: modified_base
<222> LOCATION: (24)..(25)
<223> OTHER INFORMATION: i
<221> NAME/KEY: modified_base
<222> LOCATION: (29)..(30)
<223> OTHER INFORMATION: i
<221> NAME/KEY: modified_base
<222> LOCATION: (33)..(34)
<223> OTHER INFORMATION: i

<400> SEQUENCE: 9
ggccacgcgt gcactagtac gggnngggnn ggnngg                               36

<210> SEQ ID NO 10
<211> LENGTH: 26
<212> TYPE: PRT
```

```
<213> ORGANISM: Artificial Sequence
<220> FEATURE:
<223> OTHER INFORMATION: Description of Artificial Sequence: Peptide of
      the catalytic subunit of human telomerase

<400> SEQUENCE: 10

Ser Glu Ala Glu Val Arg Gln His Arg Glu Ala Arg Pro Ala Leu Leu
 1               5                  10                  15

Thr Ser Arg Leu Arg Phe Ile Pro Lys Cys
            20                  25

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 11
gtaatacgac tcactcacta tagg                                              24

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 12
caggaaacag ctatgacc                                                     18

<210> SEQ ID NO 13
<211> LENGTH: 287
<212> TYPE: PRT
<213> ORGANISM: Homo sapiens

<400> SEQUENCE: 13

Met Leu Arg Ser Phe Phe Tyr Val Thr Glu Thr Thr Phe Gln Lys Asn
 1               5                  10                  15

Arg Leu Phe Phe Tyr Arg Lys Ser Val Trp Ser Lys Leu Gln Ser Ile
            20                  25                  30

Gly Arg Ile Gln His Leu Lys Arg Val Gln Leu Arg Glu Leu Ser Glu
        35                  40                  45

Ala Glu Val Arg Gln His Arg Glu Ala Arg Pro Ala Leu Leu Thr Ser
    50                  55                  60

Arg Leu Arg Phe Ile Pro Lys Pro Asp Gly Leu Arg Pro Ile Val Asn
65                  70                  75                  80

Met Asp Tyr Val Val Gly Ala Arg Thr Phe Arg Arg Glu Lys Arg Ala
                85                  90                  95

Glu Arg Leu Thr Ser Arg Val Lys Ala Leu Phe Ser Val Leu Asn Tyr
            100                 105                 110

Glu Arg Ala Arg Arg Pro Gly Leu Leu Gly Ala Ser Val Leu Gly Leu
        115                 120                 125

Asp Asp Ile His Arg Ala Trp Arg Thr Phe Val Leu Arg Val Arg Ala
    130                 135                 140

Gln Asp Pro Pro Pro Glu Leu Tyr Phe Val Lys Val Asp Val Thr Gly
145                 150                 155                 160

Ala Tyr Asp Thr Ile Pro Gln Asp Arg Leu Thr Glu Val Ile Ala Ser
                165                 170                 175
```

```
                                                                 -continued

Ile Ile Lys Pro Gln Asn Thr Tyr Ile Arg Gly Lys Ser Tyr Val Gln
            180                 185                 190

Cys Gln Gly Ile Pro Gln Gly Ser Ile Leu Ser Thr Leu Leu Cys Ser
            195                 200                 205

Leu Cys Tyr Asp Gly Met Glu Asn Lys Leu Phe Ala Gly Gly Ile Arg
    210                 215                 220

Arg Asp Gly Leu Leu Leu Arg Leu Val Asp Asp Phe Leu Leu Val Thr
225                 230                 235                 240

Pro His Leu Thr His Ala Lys Thr Phe Leu Arg Thr Leu Val Arg Gly
                245                 250                 255

Val Pro Glu Tyr Gly Cys Val Val Asn Leu Arg Lys Thr Val Val Asn
            260                 265                 270

Phe Pro Val Glu Asp Glu Ala Leu Gly Gly Thr Ala Phe Val Gln
            275                 280                 285

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 14
aatccgtcga gcagaggtt                                                    19
```